(12) United States Patent
Parker et al.

(10) Patent No.: US 10,745,439 B2
(45) Date of Patent: Aug. 18, 2020

(54) KINASE SUBSTRATES AND METHODS OF USE THEREOF

(71) Applicant: REGENTS OF THE UNIVERSITY OF MINNESOTA, Minneapolis, MN (US)

(72) Inventors: Laurie Parker, Minneapolis, MN (US); Laura Marholz, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 15/926,640

(22) Filed: Mar. 20, 2018

(65) Prior Publication Data

US 2018/0282372 A1 Oct. 4, 2018

Related U.S. Application Data

(60) Provisional application No. 62/473,775, filed on Mar. 20, 2017.

(51) Int. Cl.
| | |
|---|---|
| *C07K 7/06* | (2006.01) |
| *G01N 21/76* | (2006.01) |
| *G01N 33/573* | (2006.01) |
| *C12Q 1/48* | (2006.01) |
| *C12N 9/12* | (2006.01) |

(52) U.S. Cl.
CPC .............. *C07K 7/06* (2013.01); *C12N 9/1205* (2013.01); *C12Q 1/485* (2013.01); *G01N 21/76* (2013.01); *G01N 33/573* (2013.01); *G01N 2333/912* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 4,873,192 A | 10/1989 | Kunkel | |
| 2003/0022855 A1* | 1/2003 | Fisher | C07K 14/47 514/44 A |
| 2003/0232408 A1* | 12/2003 | Yan | C12N 9/1205 435/69.1 |
| 2007/0036793 A1* | 2/2007 | Hardie | C07K 14/82 424/146.1 |
| 2014/0220636 A1* | 8/2014 | Altermann | C07K 14/005 435/69.7 |
| 2016/0097084 A1 | 4/2016 | Parker et al. | |
| 2017/0334950 A1 | 11/2017 | Parker et al. | |
| 2019/0302117 A1 | 10/2019 | Parker et al. | |

OTHER PUBLICATIONS

UniProtKB accession No. A0A2E4J1X4, accessed Sep. 29, 2019 at URL uniprot.org/uniprot/A0A2E4J1X4, pp. 1-4 (Year: 2018).*
Baas et al., "LKB1 tumor suppressor protein: PARtaker in cell polarity," Trends Cell Biol. 14:312-319 (2004) (Year: 2004).*
Altschul, et al., "Basic local alignment search tool.", J Mol Biol 215, 403-410 (1990).

(Continued)

*Primary Examiner* — Julie Ha
*Assistant Examiner* — Kristina M Hellman
(74) *Attorney, Agent, or Firm* — Viksnins Harris Padys Malen LLP

(57) ABSTRACT

The invention provides kinase substrates and methods comprising their use.

18 Claims, 8 Drawing Sheets

Specification includes a Sequence Listing.

(56) References Cited

OTHER PUBLICATIONS

Altschul, et al., "Gapped BLAST and PSI-BLAST: a new generation of protein database search programs.", Nucleic Acids Res 25(17), 3389-3402 (1997).
Batzer, et al., "Enhanced evolutionary PCR using oligonucleotides with inosine at the 3'-terminus", Nucl Acids Res 19(18), 5081 (1991).
Corpet, et al., "Multiple sequence alignment with hierarchical clustering.", Nucl Acids Res 16, 10881-10890 (1988).
Hajduch, et al., "Protein kinase B (PKB/Akt)—a key regulator of glucose transport?", FEBS Lett 492(3), 199-203 (2001).
Hemminki, et al., "A serine/threonine kinase gene defective in Peutz-Jeghers syndrome", Nature 391(6663), 184-187 (1998).
Higgins, et al., "CLUSTAL: a package for performing multiple sequence alignment on a microcomputer", Gene 73, 237-244 (1988).
Higgins, et al., "Fast and sensitive multiple sequence alignments on a microcomputer.", CABIOS 5(2), 151-153 (1989).
Huang, et al., "Parallelization of a local similarity algorithm", CABIOS 8, 155-165 (1992).
Ji, et al., "LKB1 modulates lung cancer differentiation and metastasis", Nature 448(7155), 807-810 (2007).
Karlin, et al., "Applications and statistics for multiple high-scoring segments in molecular sequences.", Proc Natl Acad Sci 90, 5873-5877 (1993).
Karlin, et al., "Methods for assessing the statistical significance of molecular sequence features by using general scoring schemes.", Proc Natl Acad Sci 87(6), 2264-2268 (1990).
Knoechel, et al., "Metabolic Mechanisms of Drug Resistance in Leukemia", Cell Metab 22(5), 759-760 (2015).
Kunkel, "Rapid and efficient site-specific mutagenesis without phenotypic selection", Proc Natl Acad Sci USA 82, 488-492 (1985).
Kunkel, et al., "Rapid and Efficient Site-Specific Mutagenesis without Phenotypic Selection", Meth Enzymol 154, 367-382 (1987).
Lipchik, et al., "KINATEST-ID: a pipeline to develop phosphorylation-dependent terbium sensitizing kinase assays", J Am Chem Soc 137, 2484-2494 (2015).
Lizcano, et al., "LKB1 is a master kinase that activates 13 kinases of the AMPK subfamily, including MARK/PAR-1", EMBO J 23(4), 833-843 (2004).
Marholz, et al., "Investigations of kinase signaling in cancer metabolism with cell-active, kinase-specific biosensors", Poster 25, United States Human Proteome Organization (US-HUPO) Conference, San Diego, CA, 1 page (Mar. 21, 2017).
Martin, et al., "The best and the brightest: exploiting tryptophan-sensitized Tb(3+) luminescence to engineer lanthanide-binding tags", Methods Mol Biol 1248, 201-220 (2015).
Myers, et al., "Optimal alignments in linear space.", CABIOS 4(1), 11-17 (1988).
Needleman, et al., "A General Method Applicable to the Search for Similarities in the Amino Acid Sequence of Two Proteins.", J Mol Biol 48, 443-453 (1970).
Nicholson, et al., "The protein kinase B/Akt signalling pathway in human malignancy", Cell Signal 14(5), 381-395 (2002).
Ohtsuka, et al., "An Alternative Approach to Deoxyoligonucleotides as Hybridization Probes by Insertion of Deoxyinosine at Ambiguous Codon Positions", JBC 260(5), 2605-2608 (1985).
Pearson, et al., "Improved tools for biological sequence comparison.", Proc Natl Acad Sci 85, 2444-2448 (1988).
Pearson, et al., "Using the FASTA program to search protein and DNA sequence databases.", Meth Mol Biol 24, 307-331 (1994).
Robey, et al., "Is Akt the "Warburg kinase"?—Akt-energy metabolism interactions and oncogenesis", Semin Cancer Biol 19, 25-31 (2009).
Rossolini, et al., "Use of deoxyinosine-containing primers vs degenerate primers for polymerase chain reaction based on ambiguous sequence information", Mol Cell Probes 8, 91-98 (1994).
Smith, et al., "Comparison of biosequences.", Adv Appl Math 2(4), 482-489 (1981).
Sueda, et al., "A luminescent affinity tag for proteins based on the terbium(II)-binding peptide", Analytical Biochemistry 422(1), 52-54 (2012).
Whiteman, et al., "Role of Akt/protein kinase B in metabolism", Trends Endocrin Met 13(10), 444-451 (2002).
Wingo, et al., "Somatic LKB1 Mutations Promote Cervical Cancer Progression", PLoS One 4, e5137 (2009).
Yang, et al., "mTOR kinase structure, mechanism and regulation by the rapamycin-binding domain", Nature 497, 217-223 (2013).

* cited by examiner

| Amino Acid | -7 | -6 | -5 | -4 | -3 | -2 | -1 | 0 | 1 | 2 | 3 | 4 | 5 | 6 | 7 |
|---|---|---|---|---|---|---|---|---|---|---|---|---|---|---|---|
| A | -0.93 | -2.76 | -0.93 | -2.76 | -0.93 | 2.75 | 2.76 | -2.76 | -0.93 | -0.93 | 0.91 | -2.76 | -0.93 | -0.93 | -2.76 |
| C | -1.79 | 4.16 | -1.79 | -1.79 | -1.79 | 4.16 | -1.79 | -1.79 | -1.79 | -1.79 | -1.79 | -1.79 | 4.16 | -1.79 | -1.79 |
| D | 3.69 | -3.72 | -3.72 | 7.39 | -3.72 | -3.72 | 3.69 | -3.72 | -3.72 | 3.69 | -3.72 | -3.72 | -3.72 | 7.39 | -0.02 |
| E | -3.14 | -0.86 | -3.72 | 1.41 | -0.86 | -3.14 | -3.14 | -3.14 | -3.14 | -0.86 | -3.14 | -3.14 | -3.14 | -0.86 | -3.14 |
| F | 1.52 | -2.79 | 5.83 | 5.83 | 10.14 | -2.79 | 10.14 | -2.79 | 1.52 | -2.79 | -2.79 | 1.81 | 5.83 | 1.52 | 5.83 |
| G | 1.81 | 1.81 | 1.81 | -3.65 | -0.92 | 1.81 | 4.55 | -3.65 | -3.65 | 4.55 | 4.55 | 1.81 | -0.92 | -3.65 | -3.65 |
| H | -2.23 | -2.23 | 1.87 | -2.23 | -2.23 | -2.23 | -2.23 | -2.23 | -2.23 | -2.23 | -2.23 | -2.23 | 1.87 | -2.23 | 1.87 |
| I | -2.66 | 3.32 | -2.66 | -2.66 | -2.66 | 0.33 | -2.66 | -2.66 | -2.66 | -2.66 | 0.33 | 3.32 | 0.33 | 0.33 | 0.33 |
| K | 3.25 | -1.98 | -1.98 | 1.51 | -1.98 | -0.23 | -0.23 | -1.98 | -0.23 | -0.23 | -0.23 | -0.23 | -1.98 | -1.98 | 1.51 |
| L | -1.77 | -3.73 | -1.77 | -1.77 | 6.07 | -1.77 | -1.77 | -3.73 | 6.07 | 0.19 | 0.19 | 4.11 | 0.19 | -1.77 | -1.77 |
| M | -2.44 | -2.44 | 2.76 | -2.44 | -2.44 | -2.44 | -2.44 | -2.44 | -2.44 | -2.44 | -2.44 | -2.44 | -2.44 | -2.44 | -2.44 |
| N | -1.95 | -1.95 | -1.95 | -1.95 | -1.95 | -1.95 | -1.95 | -1.95 | -1.95 | 0.94 | 0.94 | -1.95 | -1.95 | 0.94 | 0.94 |
| P | 3.84 | -0.55 | -0.55 | -2.01 | -2.01 | 0.91 | 0.91 | -2.01 | -2.39 | 3.84 | -0.55 | 0.91 | -0.55 | 0.91 | 3.84 |
| Q | -2.39 | 0.11 | 2.61 | 2.61 | -2.39 | -2.39 | -2.39 | -2.39 | -2.39 | -2.39 | -2.39 | -2.39 | -2.39 | -2.39 | -2.39 |
| R | -2.90 | 2.18 | -0.36 | -0.36 | 4.72 | -2.90 | -2.90 | -2.90 | -2.90 | -0.36 | -0.36 | -2.90 | 2.18 | -2.90 | -2.90 |
| S | 9.64 | 9.64 | -1.62 | 5.13 | 0.63 | 11.89 | 2.88 | 34.41 | -1.62 | -1.62 | 5.13 | 5.13 | 2.88 | 5.13 | 7.39 |
| T | 4.54 | 3.34 | 3.34 | -0.60 | 3.34 | -4.54 | 3.34 | 7.27 | -0.60 | 7.27 | -0.60 | 7.27 | 3.34 | 3.34 | -4.54 |
| V | -3.05 | -0.53 | 4.52 | 8.42 | -3.05 | 2.00 | -3.05 | -3.05 | -3.05 | -3.05 | 2.00 | -0.53 | 4.52 | 5.10 | 2.00 |
| W | -1.27 | -1.27 | -1.27 | -1.27 | -1.27 | -1.27 | -1.27 | -1.27 | -1.27 | -1.27 | -1.27 | -1.27 | -1.27 | -1.27 | -1.27 |
| Y | -1.94 | 2.00 | -1.94 | 2.00 | 5.93 | -1.94 | -1.94 | -1.94 | 2.00 | -1.94 | 2.00 | -1.94 | -1.94 | 2.00 | -1.94 |

FIGURE 6

| Amino Acid | -7 | -6 | -5 | -4 | -3 | -2 | -1 | 0 | 1 | 2 | 3 | 4 | 5 | 6 | 7 |
|---|---|---|---|---|---|---|---|---|---|---|---|---|---|---|---|
| A | 0.81 | -1.31 | -1.91 | -0.70 | -2.52 | -0.10 | 0.81 | -2.82 | -0.69 | -0.40 | -1.91 | 0.21 | -2.21 | -0.08 | -0.38 |
| C | 0.45 | -0.27 | -0.27 | -1.00 | -1.72 | -1.00 | 0.45 | -1.72 | -0.99 | -1.00 | 0.45 | -0.27 | -0.88 | -1.72 | -0.26 |
| D | -2.98 | 0.58 | -3.49 | -1.46 | -2.98 | -1.97 | -0.95 | -3.49 | -1.44 | 2.61 | 1.59 | -0.44 | -1.43 | -2.47 | -0.42 |
| E | -1.19 | 0.03 | -2.71 | -0.89 | -2.71 | -2.41 | -1.80 | -3.02 | -0.26 | -0.58 | 0.63 | -0.89 | 1.00 | -1.48 | -0.56 |
| F | -0.82 | 2.90 | -2.07 | -2.07 | -2.69 | -1.44 | -0.82 | -2.69 | 2.94 | -2.07 | 1.66 | -0.82 | 0.47 | -0.81 | 1.07 |
| G | 0.74 | 0.74 | -1.63 | 0.51 | -2.11 | -0.92 | 0.51 | -2.11 | -0.91 | 0.98 | 0.27 | 0.03 | 1.03 | -0.67 | 0.05 |
| H | -1.73 | 0.64 | -0.94 | -0.15 | -1.73 | 0.64 | 2.22 | -2.52 | -0.93 | -1.73 | 0.64 | 3.01 | -0.91 | -2.52 | -0.13 |
| I | 0.20 | 0.20 | -1.57 | 0.64 | -2.46 | -2.01 | 0.64 | -2.46 | 0.67 | -0.24 | -0.69 | -1.57 | -0.88 | 0.67 | -0.67 |
| K | 0.07 | 0.41 | -1.33 | 1.46 | -0.28 | 1.81 | 0.07 | -2.73 | -2.02 | -0.98 | -1.68 | -0.63 | 0.11 | 1.49 | 0.44 |
| L | 0.33 | -1.90 | -2.54 | -1.26 | -3.81 | 0.33 | -0.95 | -3.81 | 2.28 | -1.90 | 0.96 | -1.26 | -1.22 | -1.24 | -0.80 |
| M | -0.15 | 0.63 | -1.71 | -0.15 | -2.49 | 2.20 | -0.93 | -2.49 | 3.81 | -0.15 | -0.93 | -1.71 | -2.49 | -0.13 | -0.92 |
| N | -1.03 | 0.14 | -2.79 | 0.73 | -2.21 | 0.73 | 2.40 | -2.79 | 0.76 | 1.91 | -0.44 | 0.14 | -0.41 | -1.61 | -1.61 |
| P | 0.52 | 0.27 | -1.23 | 1.53 | -1.99 | -0.73 | -0.73 | -2.24 | -0.47 | 1.53 | -0.73 | -0.23 | 1.58 | 0.29 | -0.21 |
| Q | 1.40 | -0.17 | -1.35 | -0.56 | -2.52 | -1.35 | -1.35 | -2.52 | -1.73 | -0.95 | -0.95 | 0.22 | -0.93 | 0.24 | 0.64 |
| R | 2.79 | 0.00 | 29.68 | 4.54 | 37.70 | 3.49 | 2.10 | 25.10 | -1.03 | 0.70 | -0.70 | 1.40 | 2.17 | 1.78 | 1.43 |
| S | -0.44 | -0.18 | -2.43 | -0.44 | -2.71 | 4.67 | 0.70 | 10.43 | -0.70 | 1.83 | 4.10 | 2.97 | 1.91 | 3.01 | 1.30 |
| T | 1.69 | 0.63 | -1.51 | -1.51 | -3.64 | 0.63 | 0.09 | -3.48 | -1.49 | 0.63 | -0.97 | 1.16 | -0.39 | 0.66 | -2.03 |
| V | -2.05 | -0.15 | -3.01 | -1.50 | -3.48 | -1.58 | -0.15 | -3.48 | 3.72 | -1.58 | -0.15 | -2.05 | -0.10 | 1.32 | 1.32 |
| W | -1.50 | -1.50 | -0.37 | -1.50 | -1.50 | -1.50 | -1.50 | -1.50 | 0.40 | -1.50 | -0.37 | -0.37 | 0.79 | -0.36 | -0.36 |
| Y | -1.69 | -1.01 | -1.69 | -0.34 | -1.69 | -2.37 | -1.01 | -2.37 | -0.32 | -1.01 | -2.37 | 0.34 | -2.37 | -0.32 | 0.36 |

KINASE SUBSTRATES AND METHODS OF USE THEREOF

RELATED APPLICATION

This application claims the benefit of priority of U.S. Provisional Application Ser. No. 62/473,775 filed on Mar. 20, 2017, which application is incorporated by reference herein.

GOVERNMENT FUNDING

This invention was made with government support under CA182543 awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 27, 2018, is named 09531_435US1_SL.txt and is 4,508 bytes in size.

BACKGROUND

Alterations in the metabolism of cancerous cells have been well established and include the upregulated intake of glucose and nutrients, and the enhanced reliance on aerobic glycolysis (the so-called "Warburg effect"). These changes may help cancer cells proliferate and survive stressful conditions, and may even help explain the development of drug resistance to commonly prescribed cancer treatments. It is important to investigate the mechanisms of these metabolic changes by studying the signaling activity of serine/threonine kinases that are intimately involved in regulating aspects of metabolism (e.g., LKB1, AMPK, mTOR, and Akt).

Currently there is a need for new compounds and compositions to study specific kinases, such as LKB1, AMPK, mTOR, and Akt. Specifically, new substrates that may be used to evaluate the activity of LKB1, AMPK, mTOR and Akt are needed.

SUMMARY OF THE INVENTION

Thus, described herein are certain peptides that may be used as biosensors to, e.g., study the signaling activity of a panel of serine/threonine kinases (e.g., LKB1, AMPK, mTOR and Akt). For example, these biosensors may be used to investigate the mechanisms of metabolic changes in cells, such as in a drug-resistant chronic myeloid leukimia (CIVIL) cell line. As described herein, these peptidic biosensors are designed using the KINATEST-ID platform. The biosensors are compatible for high-throughput experiments and live-cell applications and may be used as chemical tools to quantitatively measure the signaling activity of these kinases in cells, such as drug-sensitive CML cell lines, as well as those cultured specifically for drug resistances to imatinib, nilotinib, and dasatinib.

Accordingly, certain embodiments of the invention provide a peptide comprising an amino acid sequence having at least about 85% sequence identity to formula I:

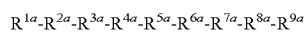
(I)

wherein:
$R^{1a}$ is any amino acid;
$R^{2a}$ is any amino acid;
$R^{3a}$ is L;
$R^{4a}$ is selected from the group consisting of: D, M, Q, T, and Y;
$R^{5a}$ is T;
$R^{6a}$ is any amino acid;
$R^{7a}$ is C;
$R^{8a}$ is selected from the group consisting of: G and I; and
$R^{9a}$ is any amino acid;
or a salt thereof. In certain embodiments, such a peptide is a Liver Kinase B1 (LKB1) substrate.

Certain embodiments of the invention provide a peptide comprising an amino acid sequence having at least about 85% sequence identity to formula II:

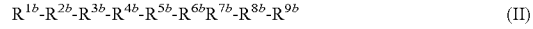
(II)

wherein:
$R^{1b}$ is selected from the group consisting of: H, P, R, and S;
$R^{2b}$ is R;
$R^{3b}$ is selected from the group consisting of: M, R, S, and T;
$R^{4b}$ is selected from the group consisting of: D, H, and T;
$R^{5b}$ is selected from the group consisting of: S and T;
$R^{6b}$ is selected from the group consisting of: H, Q, S, T, and Y;
$R^{7b}$ is selected from the group consisting of: A, P, Q, and S;
$R^{8b}$ is selected from the group consisting of: D, H, N, S, T, and W; and
$R^{9b}$ is selected form the group consisting of: F, L, and V;
or a salt thereof. In certain embodiments, such a peptide is an AMP-activated protein kinase (AMPK) substrate.

Certain embodiments of the invention provide a peptide comprising an amino acid sequence having at least about 85% sequence identity to formula IV:

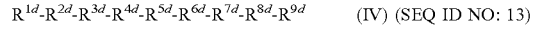
(IV) (SEQ ID NO: 13)

wherein:
$R^{1d}$ is R;
$R^{2d}$ is R;
$R^{3d}$ is selected from the group consisting of: M, R, and S;
$R^{4d}$ is selected from the group consisting of: H, N, and R;
$R^{5d}$ is selected from the group consisting of: S and T;
$R^{6d}$ is selected from the group consisting of: F, L, M, V, and W;
$R^{7d}$ is D;
$R^{8d}$ is S; and
$R^{9d}$ is selected form the group consisting of: H and S;
or a salt thereof. In certain embodiments, such a peptide is a protein kinase B (Akt) substrate.

Certain embodiments of the invention provide a peptide comprising an amino acid sequence having at least about 85% sequence identity to formula IV:

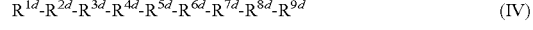
(IV)

wherein:
$R^{1d}$ is R;
$R^{2d}$ is R;
$R^{3d}$ is selected from the group consisting of: M, R, and S;
$R^{4d}$ is selected from the group consisting of: H, N, and R;
$R^{5d}$ is selected from the group consisting of: S and T;
$R^{6d}$ is selected from the group consisting of: F, L, M, V, and W;
$R^{7d}$ is D;

$R^{8d}$ is S; and $R^{9d}$ is selected form the group consisting of: H and S;

or a salt thereof. In certain embodiments, such a peptide is a protein kinase B (Akt) substrate.

Certain embodiments of the invention provide a nucleic acid sequence encoding a peptide as described herein.

Certain embodiments of the invention provide a composition comprising one or more peptides as described herein and a kinase.

Certain embodiments of the invention provide a composition comprising one or more peptides as described herein and a lanthanide metal.

Certain embodiments of the invention provide a composition comprising one or more peptides as described herein, a kinase, and optionally a detectable agent (e.g., a lanthanide metal).

Certain embodiments of the invention provide a complex comprising one or more peptides as described herein and a lanthanide metal.

Certain embodiments of the invention provide a method for detecting the activity of a kinase comprising:

1) contacting the kinase with a peptide as described herein to provide a resulting mixture;

2) contacting the resulting mixture with a lanthanide metal, under conditions such that a luminescent signal from the lanthanide metal is generated; and 3) detecting the luminescent signal, wherein the luminescent signal correlates with the activity of the kinase.

Certain embodiments of the invention provide a method to identify an inhibitor of a kinase comprising:

1) contacting a peptide as described herein, the kinase, and a test compound to provide a resulting mixture;

2) contacting the resulting mixture with a lanthanide metal; and 3) detecting a luminescent signal from the lanthanide metal, wherein the luminescent signal from the lanthanide metal correlates with the ability of the test compound to inhibit to the kinase.

The invention also provides processes and intermediates disclosed herein that are useful for preparing a peptide as described herein, or a salt thereof.

BRIEF DESCRIPTION OF THE FIGURES

FIG. 3 illustrates the amino acid preferences at positions −7 to +7 surrounding the serine/threonine phosphosite for LKB1. These preferences are based on the frequencies of amino acids at each position in sequence libraries of endogenous substrates in comparison to the amino acid frequencies expected in background (whole substrate proteins+non-phosphorylated interactors). Values greater than 2 are considered preferable for the kinase while those less than −2 are considered unfavorable. The preferred amino acids at the highly important −4 to +4 region around the phosphosite for LKB1 are shown at the bottom.

FIG. 4 illustrates the amino acid preferences at positions −7 to +7 surrounding the serine/threonine phosphosite for AMPK. These preferences are based on the frequencies of amino acids at each position in sequence libraries of endogenous substrates in comparison to the amino acid frequencies expected in background (whole substrate proteins+non-phosphorylated interactors). Values greater than 2 are considered preferable for the kinase while those less than −2 are considered unfavorable. The preferred amino acids at the highly important −4 to +4 region around the phosphosite for AMPK are shown at the bottom.

FIG. 5 illustrates the amino acid preferences at positions −7 to +7 surrounding the serine/threonine phosphosite for mTOR. These preferences are based on the frequencies of amino acids at each position in sequence libraries of endogenous substrates in comparison to the amino acid frequencies expected in background (whole substrate proteins+non-phosphorylated interactors). Values greater than 2 are considered preferable for the kinase while those less than −2 are considered unfavorable. The preferred amino acids at the highly important −4 to +4 region around the phosphosite for mTOR are shown at the bottom.

FIG. 6 illustrates the amino acid preferences at positions −7 to +7 surrounding the serine/threonine phosphosite for Akt. These preferences are based on the frequencies of amino acids at each position in sequence libraries of endogenous substrates in comparison to the amino acid frequencies expected in background (whole substrate proteins+non-phosphorylated interactors). Values greater than 2 are considered preferable for the kinase while those less than −2 are considered unfavorable. The preferred amino acids at the highly important −4 to +4 region around the phosphosite for Akt are shown at the bottom (SEQ ID NO: 13).

FIG. 8A. Results from an initial kinase assay with LKB1 testing candidate biosensor peptide substrate WHLQTWCGYGGK$_{biotin}$GG (SEQ ID NO:12). The data shown is the abundance of the peptide and its phosphorylated version (SEQ ID NO:14) after incubation with the kinase for 3 hr. FIG. 8B. Zoomed in version of the spectrum showing relative abundance.

DETAILED DESCRIPTION

Figure 1A:
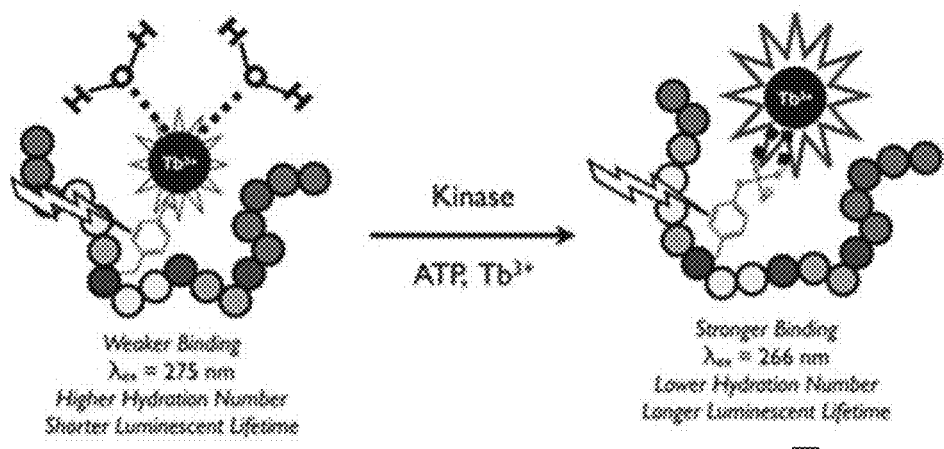
FIGS. 1A-1B illustrates using a peptidic biosensor (FIG. 1A) to detect the activity of a specific kinase through a lanthanide luminescent readout (FIG. 1B) (Lipchik A. M., et al. *J. Am. Chem. Soc.*, 2015, 137, 2484-2494).
Figure 1B:
Figure 1B:
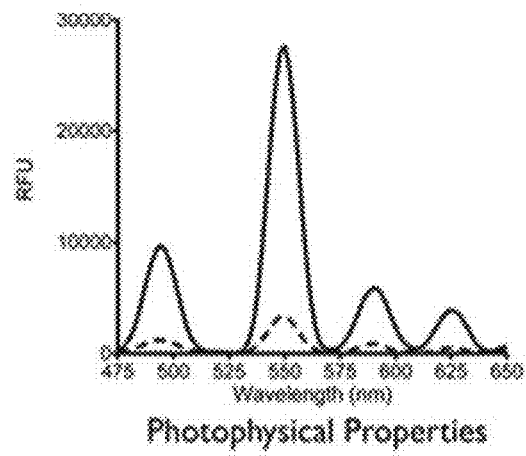

Described herein are methods for the discovery of cell-active, peptidic biosensors of specific metabolically-relevant kinases, which may be used to measure the activity of these proteins in living cells. These peptides may be rationally designed through a bioinformatics approach, which transforms an input library of verified substrate sequences to an output set of specific candidate biosensor sequences based on a statistical analysis of amino acid preferences at positions neighboring the phosphosite. These biosensors may be used in high-throughput experiments and live-cell applications. Differences in reported metabolic kinase signaling may be indicative of increased reliance on metabolic alterations, which could give insight into why this resistance occurs, and provide information on how to best counteract it. The drug-resistant CML model system is also being tested with re-sensitization strategies to determine if targeting metabolic pathways would be a viable clinical path forward for resistant patients. Knowledge of differential metabolic pathway regulation could provide novel therapeutic targets, which might be broadly applicable as many cancers are known to acquire drug resistance to many currently prescribed first-line clinical treatments.

Accordingly, certain embodiments of the invention provide peptides that are substrates of Liver Kinase B1 (LKB1), AMP-activated protein kinase (AMPK), mechanistic target of rapamycin serine/threonine kinase (mTOR) and/or protein kinase B (Akt) substrate.

Liver kinase B1 (LKB1) has been described as a master kinase, regulating AMPK and others, and an important tumor suppressor protein (Lizcano J. M., et al. *EMBO J.* 2004, 23, 833-843). Mutations in its gene were first discovered to be causative in Peutz-Jeghers syndrome, a hereditary disorder predisposing the patient to cancer (Hemminki A., et al. *Nature* 1998, 391, 184-187). More recently, it was discovered to be mutated in 15-35% of multiple subtypes of non-small cell lung carcinomas (Ji H., et al. *Nature,* 2007, 448, 807-810), and also in 20% of cervical carcinomas (Wingo S. N., et al. *PLoS One,* 2009, 4, e5137).

AMP-activated protein kinase (AMPK) is a major energy sensor and hence a metabolic master regulator. High AMP levels correspond to low energy conditions and AMPK is responsible for the activation of many downstream processes for corrective measures. The role of this kinase in cancer is controversial, and may depend on the exact context.

Mechanistic target of rapamycin (mTOR) serine/threonine kinase is another master regulator of metabolism, but in a complementary way to AMPK. It is activated under conditions of high energy and abundant nutrients, and acts to upregulate many cell growth and proliferative pathways (Yang H., et al. *Nature,* 2013, 497, 217-224.).

Protein kinase B (Akt) has hundreds of downstream targets which affect many aspects of metabolism including glucose uptake and transport, activation of the glycolysis pathway enzymes like phosphofructokinase 2 (PFK2), and regulating glycogen synthesis through inactivation of glycogen-synthase kinase 3 (Hajduch E., et al. *FEBS Lett.,* 2001, 492, 199-203; and Whiteman E. L., et al. *Trends Endocrin. Met.,* 2002, 13, 10, 444-451). There is active discussion in the literature about many aspects of this kinase, including possible connection to the Warburg effect and its involvement in drug-resistant leukemia and other human cancers (Nicholson K. M., et al. *Cell. Signal.,* 2002, 14, 381-395; Robey R., et al. *Semin. Cancer Biol.,* 2009, 19, 25-31; Knoechel B., et al. *Cell Metab.,* 2015, 22, 5, 759-760).

In certain embodiments, the peptide is a Liver Kinase B1 (LKB1) substrate. In certain embodiments, such a peptide comprises an amino acid sequence of formula I, as described below.

In certain embodiments, the peptide is an AMP-activated protein kinase (AMPK) substrate. In certain embodiments, such a peptide comprises an amino acid sequence of formula II, as described below.

In certain embodiments, the peptide is a mechanistic target of rapamycin serine/threonine kinase (mTOR) substrate. In certain embodiments, such a peptide comprises an amino acid sequence of formula III, as described below.

In certain embodiments, the peptide is a protein kinase B (Akt). In certain embodiments, such a peptide comprises an amino acid sequence of formula IV, as described below.

The peptide sequences identified and described herein can be prepared using standard techniques.

Typically, a peptide of the invention is about 9 to about 15 amino acids in length. For example, in certain embodiments, the peptide is 9 amino acids in length. In certain embodiments, the peptide is 10 amino acids in length. In certain embodiments, the peptide is 11 amino acids in length. In certain embodiments, the peptide is 12 amino acids in length. In certain embodiments, the peptide is 13 amino acids in length. In certain embodiments, the peptide is 14 amino acids in length. In certain embodiments, the peptide is 15 amino acids length. However, the length of the peptide is not critical, provided it can act as a substrate for the kinase, and as such, may be longer or shorter. Accordingly, in certain embodiments, the peptide is about 5 to about 1000 amino acids in length. In certain embodiments, the peptide is about 5 to about 500 amino acids in length. In certain embodiments, the peptide is about 5 to about 250 amino acids in length. In certain embodiments, the peptide is about 5 to about 150 amino acids in length. In certain embodiments, the peptide is about 5 to about 100 amino acids in length. In certain embodiments, the peptide is about 5 to about 75 amino acids in length. In certain embodiments, the peptide is about 5 to about 50 amino acids in length. In certain embodiments, the peptide is about 5 to about 25 amino acids in length. In certain embodiments, the peptide is about 5 to about 20 amino acids in length.

In certain embodiment, a peptide of the invention comprises/consists of an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence described herein.

In certain embodiments, a peptide of the invention comprises one or more D-amino acids. In certain embodiments, a peptide of the invention comprises one or more non-natural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine).

In certain embodiments, a peptide as described herein is capable of forming a complex with a lanthanide metal. In certain embodiments, the lanthanide metal is selected from the group consisting of La, Ce, Pr, Nd, Pm, Sm, Eu, Gd, Tb, Dy, Ho, Er, Tm, Yb, and Lu. In certain embodiments, the lanthanide metal is Tb.

Certain embodiments, of the invention provide a peptide as described herein.

Certain embodiments, of the invention provide a peptide generated using a method described herein.

Certain embodiments of the invention provide a cell comprising a peptide as described herein.

Certain embodiments of the invention also provide a nucleic acid sequence encoding a peptide as described herein.

Certain embodiments of the invention provide an expression cassette comprising a nucleic acid as described herein operably linked to a promoter.

Certain embodiments of the invention provide a vector comprising an expression cassette as described herein.

Certain embodiments of the invention provide a cell comprising a vector as described herein.

Peptides Comprising Formula I (e.g., Substrates of LKB1)

Certain embodiments of the invention provide a peptide comprising an amino acid sequence of formula I:

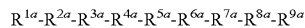    (I)

$R^{1a}\text{-}R^{2a}\text{-}R^{3a}\text{-}R^{4a}\text{-}R^{5a}\text{-}R^{6a}\text{-}R^{7a}\text{-}R^{8a}\text{-}R^{9a}$ wherein:
R$^{1a}$ is any amino acid;
R$^{2a}$ is any amino acid;
R$^{3a}$ is L;
R$^{4a}$ is selected from the group consisting of: D, M, Q, T, and Y;
R$^{5a}$ is T;
R$^{6a}$ is any amino acid;
R$^{7a}$ is C;
R$^{8a}$ is selected from the group consisting of: G and I; and
R$^{9a}$ is any amino acid;
or a salt thereof.

As used herein, the term "any amino acid" includes both natural and non-natural amino acids, in D or L form.

In certain embodiments, R$^{4a}$ is D. In certain embodiments, R$^{4a}$ is M. In certain embodiments, R$^{4a}$ is Q. In certain embodiments, R$^{4a}$ is T. In certain embodiments, R$^{4a}$ is Y.

In certain embodiments, R$^{8a}$ is G. In certain embodiments, R$^{8a}$ is I.

In certain embodiments, a peptide comprises an amino acid sequence of formula I, wherein:
R$^{1a}$ is any amino acid;
R$^{2a}$ is any amino acid;
R$^{3a}$ is L;
R$^{4a}$ is Q;
R$^{5a}$ is T;
R$^{6a}$ is any amino acid;
R$^{7a}$ is C;
R$^{8a}$ is G; and
R$^{9a}$ is any amino acid;
or a salt thereof.

In certain embodiments, a peptide comprises an amino acid sequence of formula I, wherein:
R$^{1a}$ is selected from the group consisting of: D, E, K, N, S, W, and Y;
R$^{2a}$ is selected from the group consisting of: F, H, K, L;
R$^{3a}$ is L;
R$^{4a}$ is selected from the group consisting of: D, M, Q, T, and Y;
R$^{5a}$ is T;
R$^{6a}$ is selected from the group consisting of: C, F, S, and W;
R$^{7a}$ is C;
R$^{8a}$ is selected from the group consisting of: G and I; and
R$^{9a}$ is selected form the group consisting of: S, T, and Y;
or a salt thereof.

In certain embodiments, R$^{1a}$ is D. In certain embodiments, R$^{1a}$ is E. In certain embodiments, R$^{1a}$ is K. In certain embodiments, R$^{1a}$ is N. In certain embodiments, R$^{1a}$ is S. In certain embodiments, R$^{1a}$ is W. In certain embodiments, R$^{1a}$ is Y. In certain embodiments, R$^{1a}$ is N or W.

In certain embodiments, R$^{2a}$ is F. In certain embodiments, R$^{2a}$ is H. In certain embodiments, R$^{2a}$ is K. In certain embodiments, R$^{2a}$ is L. In certain embodiments, R$^{2a}$ is F, K or L.

In certain embodiments, R$^{4a}$ is D. In certain embodiments, R$^{4a}$ is M. In certain embodiments, R$^{4a}$ is Q. In certain embodiments, R$^{4a}$ is T. In certain embodiments, R$^{4a}$ is Y. In certain embodiments, R$^{4a}$ is D or Q.

In certain embodiments, R$^{6a}$ is C. In certain embodiments, R$^{6a}$ is F. In certain embodiments, R$^{6a}$ is S. In certain embodiments, R$^{6a}$ is W. In certain embodiments, R$^{6a}$ is F, S or W.

In certain embodiments, R$^{8a}$ is G. In certain embodiments, R$^{8a}$ is I.

In certain embodiments, R$^{9a}$ is S. In certain embodiments, R$^{9a}$ is T. In certain embodiments, R$^{9a}$ is Y. In certain embodiments, R$^{9a}$ is T or S.

In certain embodiments, the peptide comprises an amino acid sequence of formula I: wherein:
R$^{1a}$ is selected from the group consisting of: D, E, K, N, S, W, and Y;
R$^{2a}$ is selected from the group consisting of: F, H, K, L;
R$^{3a}$ is L;
R$^{4a}$ is Q.
R$^{5a}$ is T;
R$^{6a}$ is selected from the group consisting of: C, F, S, and W;
R$^{7a}$ is C;
R$^{8a}$ is G; and
R$^{9a}$ is selected form the group consisting of: S, T, and Y;
or a salt thereof.

In certain embodiments, the peptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to WHLQTWCGS (SEQ ID NO:5). In certain embodiments, the peptide comprises amino acid sequence WHLQTWCGS (SEQ ID NO:5), or a salt thereof. In certain embodiments, the peptide consists of an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to WHLQTWCGS (SEQ ID NO:5). In certain embodiments, the peptide consists of amino acid sequence WHLQTWCGS (SEQ ID NO:5), or a salt thereof.

In certain embodiments, the peptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to WHLQTWCGY (SEQ ID NO:6). In certain embodiments, the peptide comprises amino acid sequence WHLQTWCGY (SEQ ID NO:6), or a salt thereof. In certain embodiments, the peptide consists of an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to WHLQTWCGY (SEQ ID NO:6). In certain embodiments, the peptide consists of amino acid sequence WHLQTWCGY (SEQ ID NO:6), or a salt thereof.

In certain embodiments, a peptide comprises an amino acid sequence of formula I, wherein:
R$^{1a}$ is N or W;
R$^{2a}$ is F, K or L;
R$^{3a}$ is L;
R$^{4a}$ is D or Q;
R$^{5a}$ is T;
R$^{6a}$ is F, S or W;
R$^{7a}$ is C;
R$^{8a}$ is G; and
R$^{9a}$ is T or S;
or a salt thereof.

In certain embodiments, a peptide as described herein further comprises an amino acid sequence of formula Ia:

$$W^{1a}\text{-}W^{2a}\text{-}W^{3a} \tag{Ia}$$

or a salt thereof, wherein:
the C'terminus of the amino acid sequence of formula Ia is operably linked the N'terminus of the amino acid sequence of formula I;
W$^{1a}$ is selected from the group consisting of: absent, H, K, Q, T, and V;

$W^{2a}$ is selected from the group consisting of: absent, D, G, P, V, and W; and $W^{3a}$ is selected form the group consisting of: D and G.

In certain embodiments, a peptide as described herein further comprises an amino acid sequence of formula Ia, wherein:

$W^{1a}$ is selected from the group consisting of: H, K, Q, T, and V;

$W^{2a}$ is selected from the group consisting of: D, G, P, V, and W; and $W^{3a}$ is selected form the group consisting of: D and G.

In certain embodiments, $W^{1a}$ is absent. In certain embodiments, $W^{1a}$ is H. In certain embodiments, $W^{1a}$ is K. In certain embodiments, $W^{1a}$ is Q. In certain embodiments, $W^{1a}$ is T. In certain embodiments, $W^{1a}$ is V.

In certain embodiments, $W^{2a}$ is absent. In certain embodiments, $W^{2a}$ is D. In certain embodiments, $W^{2a}$ is G. In certain embodiments, $W^{2a}$ is P. In certain embodiments, $W^{2a}$ is V. In certain embodiments, $W^{2a}$ is W.

In certain embodiments, $W^{3a}$ is D. In certain embodiments, $W^{3a}$ is G.

In certain embodiments, a peptide as described herein further comprises an amino acid sequence of formula Ib:

$$W^{4a}\text{-}W^{5a}\text{-}W^{6a} \qquad \text{(Ib)}$$

or a salt thereof, wherein:

the C'terminus of the amino acid sequence of formula I is operably linked to the N'terminus of the amino acid sequence of formula Ib;

$W^{4a}$ is selected from the group consisting of: L and P;

$W^{5a}$ is selected from the group consisting of: absent, H and P; and $W^{6a}$ is absent or Y.

In certain embodiments, a peptide as described herein further comprises an amino acid sequence of formula Ib, wherein:

$W^{4a}$ is selected from the group consisting of: L and P;

$W^{5a}$ is selected from the group consisting of: H and P; and $W^{6a}$ is Y.

In certain embodiments, $W^{4a}$ is L. In certain embodiments, $W^{4a}$ is P.

In certain embodiments, $W^{5a}$ is absent. In certain embodiments, $W^{5a}$ is H. In certain embodiments, $W^{5a}$ is P.

In certain embodiments, $W^{6a}$ is absent. In certain embodiments, $W^{6a}$ is Y.

Certain embodiments of the invention provide a peptide comprising an amino acid sequence having about 65% to about 100%, about 70% to about 100%, about 71% to about 100%, about 72% to about 100%, about 73% to about 100%, about 74% to about 100%, about 75% to about 100%, about 76% to about 100%, about 77% to about 100%, about 78% to about 100%, about 79% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100% or about 98% to about 100% sequence identity to an amino acid sequence of formula I. In certain embodiments, the peptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula I. In certain embodiments, the peptide consists of an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula I. In certain embodiments, the peptide consists of an amino acid sequence of formula I.

In certain embodiments, the peptide comprises an amino acid sequence of formula Ia, formula I and formula Ib, wherein the C'terminus of the amino acid sequence of formula Ia is operably linked to the N'terminus of the amino acid sequence of formula I, and wherein the C'terminus of the amino acid sequence of formula I is operably linked to the N'terminus of the amino acid of formula Ib.

In certain embodiments, the peptide consists of amino acid sequences of formula Ia, formula I and formula Ib, wherein the C'terminus of the amino acid sequence of formula Ia is operably linked to the N'terminus of the amino acid sequence of formula I, and wherein the C'terminus of the amino acid sequence of formula I is operably linked to the N'terminus of the amino acid of formula Ib.

Figure 3:
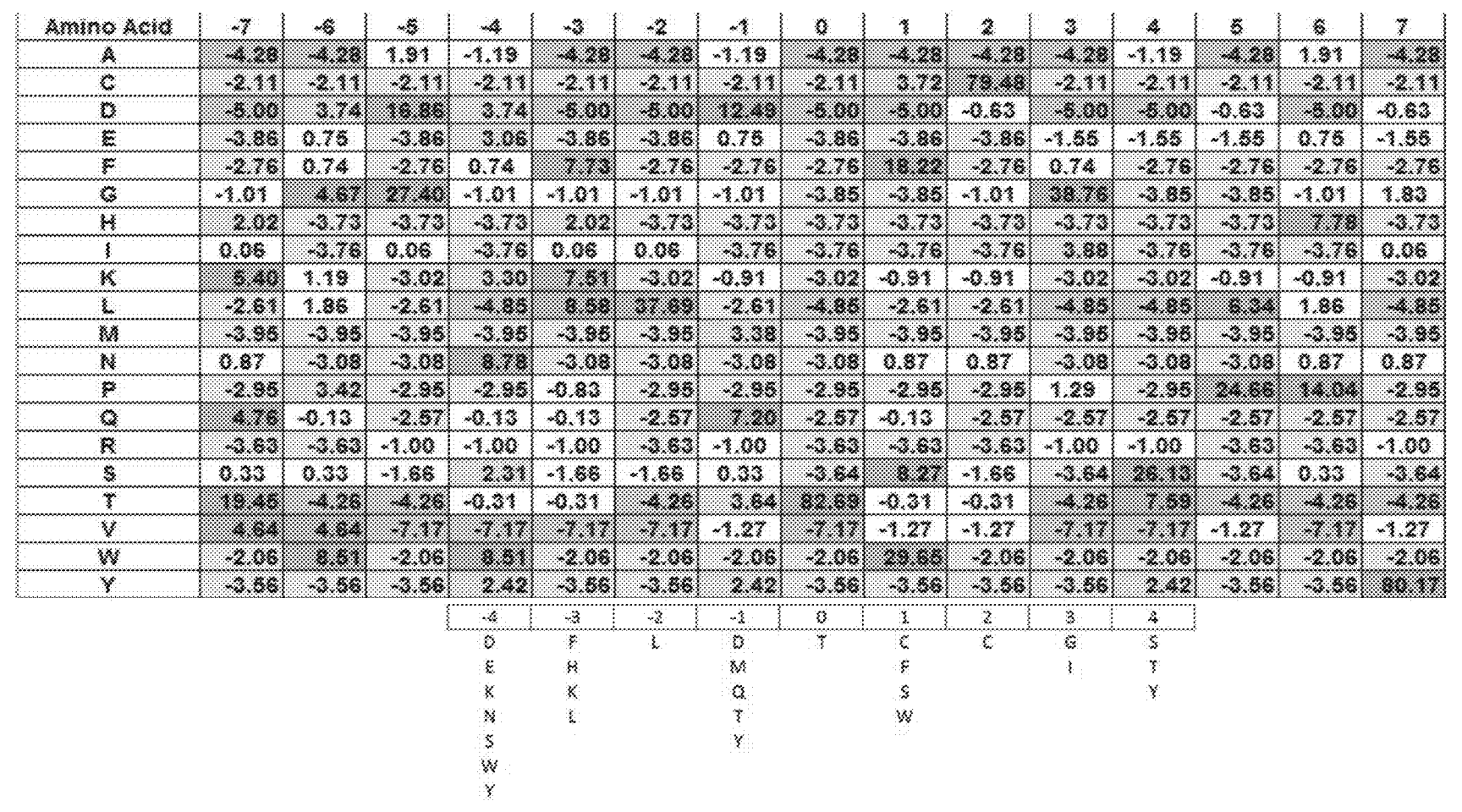

In certain embodiments, the peptide comprises an amino acid sequence selected using the information in FIG. 3.

Peptides Comprising Formula II (e.g., Substrates of AMPK)

Certain embodiments of the invention provide a peptide comprising an amino acid sequence of formula II:

$$R^{1b}\text{-}R^{2b}\text{-}R^{3b}\text{-}R^{4b}\text{-}R^{5b}\text{-}R^{6b}R^{7b}\text{-}R^{8b}\text{-}R^{9b} \qquad \text{(II)}$$

wherein:

$R^{1b}$ is selected from the group consisting of: H, P, R, and S;

$R^{2b}$ is R;

$R^{3b}$ is selected from the group consisting of: M, R, S, and T;

$R^{4b}$ is selected from the group consisting of: D, H, and T;

$R^{5b}$ is selected from the group consisting of: S and T;

$R^{6b}$ is selected from the group consisting of: H, Q, S, T, and Y;

$R^{7b}$ is selected from the group consisting of: A, P, Q, and S;

$R^{8b}$ is selected from the group consisting of: D, H, N, S, T, and W; and $R^{9b}$ is selected form the group consisting of: F, L, and V;

or a salt thereof.

In certain embodiments, $R^{1b}$ is H or R.
In certain embodiments, $R^{3b}$ is R or S.
In certain embodiments, $R^{4b}$ is D or H.
In certain embodiments, $R^{5b}$ is S.
In certain embodiments, $R^{6b}$ is H, T, or Y.
In certain embodiments, $R^{7b}$ is P or S.
In certain embodiments, $R^{8b}$ is N or S.
In certain embodiments, $R^{9b}$ is V or L.

In certain embodiments, the peptide comprises an amino acid sequence of formula II, wherein:

$R^{1b}$ is H or R;
$R^{2b}$ is R;
$R^{3b}$ is R or S;
$R^{4b}$ is D or H;
$R^{5b}$ is S;
$R^{6b}$ is H, T, or Y;
$R^{7b}$ is P or S;
$R^{8b}$ is N or S; and
$R^{9b}$ is V or L;

or a salt thereof.

In certain embodiments, $R^{1b}$ is H. In certain embodiments, $R^{1b}$ is P. In certain embodiments, $R^{1b}$ is R. In certain embodiments, $R^{1b}$ is S.

In certain embodiments, $R^{3b}$ is M. In certain embodiments, $R^{3b}$ is R. In certain embodiments, $R^{3b}$ is S. In certain embodiments, $R^{3b}$ is T.

In certain embodiments, $R^{4b}$ is D. In certain embodiments, $R^{4b}$ is H. In certain embodiments, $R^{4b}$ is T.

In certain embodiments, $R^{5b}$ is S. In certain embodiments, $R^{5b}$ is T.

In certain embodiments, $R^{6b}$ is H. In certain embodiments, $R^{6b}$ is Q. In certain embodiments, $R^{6b}$ is S. In certain embodiments, $R^{6b}$ is T. In certain embodiments, $R^{6b}$ is Y.

In certain embodiments, $R^{7b}$ is A. In certain embodiments, $R^{7b}$ is P. In certain embodiments, $R^{7b}$ is Q. In certain embodiments, $R^{7b}$ is S.

In certain embodiments, $R^{8b}$ is D. In certain embodiments, $R^{8b}$ is H. In certain embodiments, $R^{8b}$ is N. In certain embodiments, $R^{8b}$ is S. In certain embodiments, $R^{8b}$ is T. In certain embodiments, $R^{8b}$ is W.

In certain embodiments, $R^{9b}$ is F. In certain embodiments, $R^{9b}$ is L. In certain embodiments, $R^{9b}$ is V.

In certain embodiments, the peptide further comprises an amino acid sequence of formula IIa:

$$W^{1b}\text{-}W^{2b}\text{-}W^{3b} \quad \text{(IIa)}$$

or salt thereof, wherein:

the C'terminus of the amino acid sequence of formula IIa is operably linked the N'terminus of the amino acid sequence of formula II;

$W^{1b}$ is selected from the group consisting of: absent, G, P, R, and S;

$W^{2b}$ is selected from the group consisting of: absent, K, P, and T; and $W^{3b}$ is selected form the group consisting of: I, L, M, and R.

In certain embodiments, the peptide further comprises an amino acid sequence of formula IIa, wherein:

$W^{1b}$ is selected from the group consisting of: G, P, R, and S;

$W^{2b}$ is selected from the group consisting of: K, P, and T; and $W^{3b}$ is selected form the group consisting of: I, L, M, and R.

In certain embodiments, $W^{1b}$ is absent. In certain embodiments, $W^{1b}$ is G. In certain embodiments, $W^{1b}$ is P. In certain embodiments, $W^{1b}$ is R. In certain embodiments, $W^{1b}$ is S.

In certain embodiments, $W^{2b}$ is absent. In certain embodiments, $W^{2b}$ is K. In certain embodiments, $W^{2b}$ is P. In certain embodiments, $W^{2b}$ is T.

In certain embodiments, $W^{3b}$ is I. In certain embodiments, $W^{3b}$ is L. In certain embodiments, $W^{3b}$ is M. In certain embodiments, $W^{3b}$ is R.

In certain embodiments, the peptide further comprises an amino acid sequence of formula IIb:

$$W^{4b}\text{-}W^{5b}\text{-}W^{6b} \quad \text{(IIb)}$$

or a salt thereof, wherein:

the C'terminus of the amino acid sequence of formula II is operably linked to the N'terminus of the amino acid sequence of formula IIb;

$W^{4b}$ is selected from the group consisting of: H, N, R, T, and V;

$W^{5b}$ is selected from the group consisting of: absent, D, G, M, and W; and $W^{6b}$ is selected from the group consisting of: absent, L, R, and W.

In certain embodiments, the peptide further comprises an amino acid sequence of formula IIb, wherein:

$W^{4b}$ is selected from the group consisting of: H, N, R, T, and V;

$W^{5b}$ is selected from the group consisting of: D, G, M, and W; and $W^{6b}$ is selected from the group consisting of: L, R, and W.

In certain embodiments, $W^{4b}$ is H. In certain embodiments, $W^{4b}$ is N. In certain embodiments, $W^{4b}$ is R. In certain embodiments, $W^{4b}$ is T. In certain embodiments, $W^{4b}$ is V.

In certain embodiments, $W^{5b}$ is absent. In certain embodiments, $W^{5b}$ is D. In certain embodiments, $W^{5b}$ is G. In certain embodiments, $W^{5b}$ is M. In certain embodiments, $W^{5b}$ is W.

In certain embodiments, $W^{6b}$ is absent. In certain embodiments, $W^{6b}$ is L. In certain embodiments, $W^{6b}$ is R. In certain embodiments, $W^{6b}$ is W.

Certain embodiments of the invention provide a peptide comprising an amino acid sequence having about 65% to about 100%, about 70% to about 100%, about 71% to about 100%, about 72% to about 100%, about 73% to about 100%, about 74% to about 100%, about 75% to about 100%, about 76% to about 100%, about 77% to about 100%, about 78% to about 100%, about 79% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100% or about 98% to about 100% sequence identity to an amino acid sequence of formula II. In certain embodiments, the peptide comprises an amino acid sequence having about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula II. In certain embodiments, the peptide consists of an amino acid sequence having about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula II. In certain embodiments, the peptide consists of an amino acid sequence of formula II.

In certain embodiments, the peptide comprises an amino acid sequence of formula IIa, formula II and formula IIb, wherein the C'terminus of the amino acid sequence of formula IIa is operably linked to the N'terminus of the amino acid sequence of formula II, and wherein the C'terminus of the amino acid sequence of formula II is operably linked to the N'terminus of the amino acid of formula IIb.

In certain embodiments, the peptide consists of amino acid sequences of formula IIa, formula II and formula IIb, wherein the C'terminus of the amino acid sequence of formula IIa is operably linked to the N'terminus of the amino acid sequence of formula II, and wherein the C'terminus of the amino acid sequence of formula II is operably linked to the N'terminus of the amino acid of formula IIb.

Figure 4:
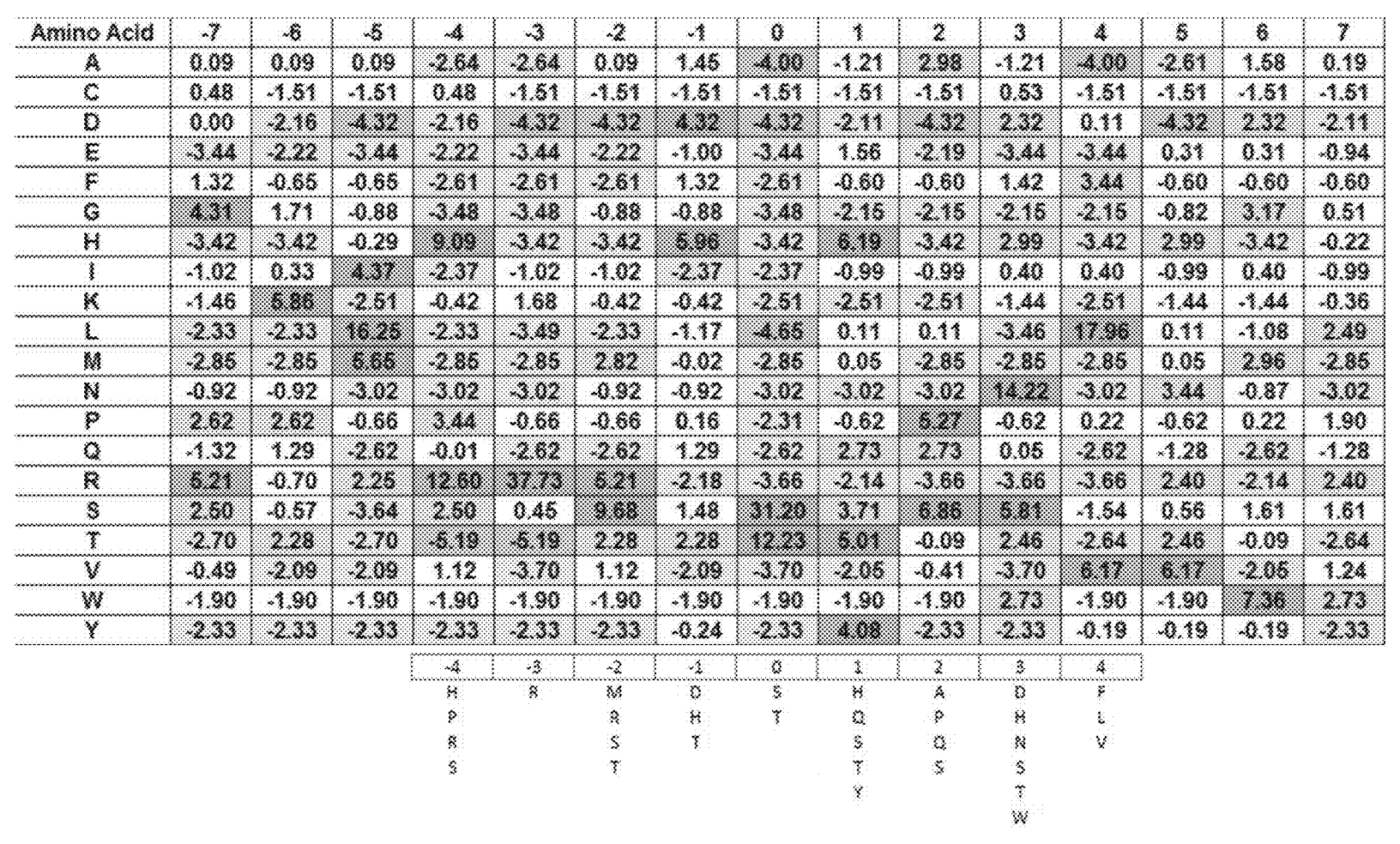

In certain embodiments, the peptide comprises an amino acid sequence selected using information in FIG. 4.

Peptides Comprising Formula III (e.g., Substrates of mTOR)

Certain embodiments of the invention provide a peptide comprising an amino acid sequence of formula III:

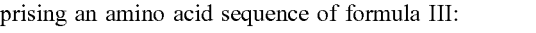

$$R^{1c}\text{-}R^{2c}\text{-}R^{3c}\text{-}R^{4c}\text{-}R^{5c}\text{-}R^{6c}\text{-}R^{7c}\text{-}R^{8c}\text{-}R^{9c} \quad \text{(III)}$$

wherein:

$R^{1c}$ is selected from the group consisting of: D, F, Q, S, and W;

$R^{2c}$ is selected from the group consisting of: F, L, R, T, and Y;

$R^{3c}$ is selected from the group consisting of: A, C, and S;

$R^{4c}$ is selected from the group consisting of: A, D, F, G, S, and T;

$R^{5c}$ is selected from the group consisting of: S and T;

$R^{6c}$ is selected from the group consisting of: L and P;

$R^{7c}$ is selected from the group consisting of: D, G, P, and T;

$R^{8c}$ is selected from the group consisting of: G and S; and $R^{9c}$ is selected form the group consisting of: I, L, S, and T;

or a salt thereof.

In certain embodiments, $R^{1c}$ is D, F, S, or W.
In certain embodiments, $R^{2c}$ is F, L, R or Y.
In certain embodiments, $R^{3c}$ is C or S.
In certain embodiments, $R^{4c}$ is F or G.
In certain embodiments, $R^{5c}$ is S or T.
In certain embodiments, $R^{6c}$ is L or P.
In certain embodiments, $R^{7c}$ is G or T.
In certain embodiments, $R^{8c}$ is G or S.
In certain embodiments, $R^{9c}$ is L, S or T.

In certain embodiments, a peptide comprises an amino acid sequence of formula III, wherein:

$R^{1c}$ is D, F, S, or W;
$R^{2c}$ is F, L, R or Y;
$R^{3c}$ is C or S;
$R^{4c}$ is F or G;
$R^{5c}$ S or T;
$R^{6c}$ is L or P;
$R^{7c}$ is G or T;
$R^{8c}$ is G or S; and
$R^{9c}$ is L, S or T;
or a salt thereof.

In certain embodiments, $R^{1c}$ is D. In certain embodiments, $R^{1c}$ is F. In certain embodiments, $R^{1c}$ is Q. In certain embodiments, $R^{1c}$ is S. In certain embodiments, $R^{1c}$ is W.

In certain embodiments, $R^{2c}$ is F. In certain embodiments, $R^{2c}$ is L. In certain embodiments, $R^{2c}$ is R. In certain embodiments, $R^{2c}$ is T. In certain embodiments, $R^{2c}$ is Y.

In certain embodiments, $R^{3c}$ is A. In certain embodiments, $R^{3c}$ is C. In certain embodiments, $R^{3c}$ is S.

In certain embodiments, $R^{4c}$ is A. In certain embodiments, $R^{4c}$ is D. In certain embodiments, $R^{4c}$ is F. In certain embodiments, $R^{4c}$ is G. In certain embodiments, $R^{4c}$ is S. In certain embodiments, $R^{4c}$ is T.

In certain embodiments, $R^{5c}$ is S. In certain embodiments, $R^{5c}$ is T.

In certain embodiments, $R^{6c}$ is L. In certain embodiments, $R^{6c}$ is P.

In certain embodiments, $R^{7c}$ is D. In certain embodiments, $R^{7c}$ is G. In certain embodiments, $R^{7c}$ is P. In certain embodiments, $R^{7c}$ is T.

In certain embodiments, $R^{8c}$ is G. In certain embodiments, $R^{8c}$ is S.

In certain embodiments, $R^{9c}$ is I. In certain embodiments, $R^{9c}$ is L. In certain embodiments, $R^{9c}$ is S. In certain embodiments, $R^{9c}$ is T.

In certain embodiments, the peptide further comprises an amino acid sequence of formula IIa:

$$W^{1c}\text{-}W^{2c}\text{-}W^{3c} \quad \text{(IIa)}$$

or a salt thereof, wherein:
the C'terminus of the amino acid sequence of formula IIa is operably linked to the N'terminus of the amino acid sequence of formula III;

$W^{1c}$ is selected from the group consisting of: absent, D, K, P and S;

$W^{2c}$ is selected from the group consisting of: absent, C, I, R, S, and T; and $W^{3c}$ is selected form the group consisting of: F, M, Q, T, and V.

In certain embodiments, the peptide further comprises an amino acid sequence of formula IIa, wherein:

$W^{1c}$ is selected from the group consisting of: D, K, P and S;

$W^{2c}$ is selected from the group consisting of: C, I, R, S, and T; and $W^{3c}$ is selected form the group consisting of: F, M, Q, T, and V.

In certain embodiments, $W^{1c}$ is absent. In certain embodiments, $W^{1c}$ is D. In certain embodiments, $W^{1c}$ is K. In certain embodiments, $W^{1c}$ is P. In certain embodiments, $W^{1c}$ is S.

In certain embodiments, $W^{2c}$ is absent. In certain embodiments, $W^{2c}$ is C. In certain embodiments, $W^{2c}$ is I. In certain embodiments, $W^{2c}$ is R. In certain embodiments, $W^{2c}$ is S. In certain embodiments, $W^{2c}$ is T.

In certain embodiments, $W^{3c}$ is F. In certain embodiments, $W^{3c}$ is M. In certain embodiments, $W^{3c}$ is Q. In certain embodiments, $W^{3c}$ is T. In certain embodiments, $W^{3c}$ is V.

In certain embodiments, the peptide further comprises an amino acid sequence of formula IIb:

$$W^{4c}\text{-}W^{5c}\text{-}W^{6c} \quad \text{(IIb)}$$

or a salt thereof, wherein:
the C'terminus of the amino acid sequence of formula III is operably linked to the N'terminus of the amino acid sequence of formula IIb;

$W^{4c}$ is selected from the group consisting of: C, F, R, S, T, and V;

$W^{5c}$ is selected from the group consisting of: absent, D, S, and T; and $W^{6c}$ is selected from the group consisting of: absent, F, P, and S.

In certain embodiments, the peptide further comprises an amino acid sequence of formula IIb, wherein:

$W^{4c}$ is selected from the group consisting of: C, F, R, S, T, and V;

$W^{5c}$ is selected from the group consisting of: D, S, and T; and $W^{6c}$ is selected from the group consisting of: F, P, and S.

In certain embodiments, $W^{4c}$ is C. In certain embodiments, $W^{4c}$ is F. In certain embodiments, $W^{4c}$ is R. In certain embodiments, $W^{4c}$ is S. In certain embodiments, $W^{4c}$ is T. In certain embodiments, $W^{4c}$ is V.

In certain embodiments, $W^{5c}$ is absent. In certain embodiments, $W^{5c}$ is D. In certain embodiments, $W^{5c}$ is S. In certain embodiments, $W^{5c}$ is T.

In certain embodiments, $W^{6c}$ is absent. In certain embodiments, $W^{6c}$ is F. In certain embodiments, $W^{6c}$ is P. In certain embodiments, $W^{6c}$ is S.

Certain embodiments of the invention provide a peptide comprising an amino acid sequence having about 65% to about 100%, about 70% to about 100%, about 71% to about 100%, about 72% to about 100%, about 73% to about 100%, about 74% to about 100%, about 75% to about 100%, about 76% to about 100%, about 77% to about 100%, about 78% to about 100%, about 79% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100% or about 98% to about 100% sequence identity to an amino acid sequence of formula III. In certain embodiments, the peptide comprises an amino acid sequence having about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula III. In certain embodiments, the peptide consists of an amino acid sequence having about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula III. In certain embodiments, the peptide consists of an amino acid sequence of formula III.

In certain embodiments, the peptide comprises an amino acid sequence of formula IIa, formula III and formula IIb, wherein the C'terminus of the amino acid sequence of formula IIa is operably linked to the N'terminus of the amino acid sequence of formula III, and wherein the C'terminus of the amino acid sequence of formula III is operably linked to the N'terminus of the amino acid of formula IIb.

In certain embodiments, the peptide consists of amino acid sequences of formula IIa, formula III and formula IIb, wherein the C'terminus of the amino acid sequence of formula IIa is operably linked to the N'terminus of the amino acid sequence of formula III, and wherein the C'terminus of the amino acid sequence of formula III is operably linked to the N'terminus of the amino acid of formula IIb.

In certain embodiments, the peptide comprises an amino acid sequence selected using information in FIG. 5.

Peptides Comprising Formula IV (e.g., Substrates of Akt)

Certain embodiments of the invention provide a peptide comprising an amino acid sequence of formula IV:

$$R^{1d}\text{-}R^{2d}\text{-}R^{3d}\text{-}R^{4d}\text{-}R^{5d}\text{-}R^{6d}\text{-}R^{7d}\text{-}R^{8d}\text{-}R^{9d} \quad \text{(IV) (SEQ ID NO: 13)}$$

wherein:
$R^{1d}$ is R;
$R^{2d}$ is R;
$R^{3d}$ is selected from the group consisting of: M, R, and S;
$R^{4d}$ is selected from the group consisting of: H, N, and R;
$R^{5d}$ is selected from the group consisting of: S and T;
$R^{6d}$ is selected from the group consisting of: F, L, M, V, and W;
$R^{7d}$ is D;
$R^{8d}$ is S; and
$R^{9d}$ is selected form the group consisting of: H and S;
or a salt thereof.

In certain embodiments, $R^{3d}$ is R or S. In certain embodiments, $R^{3d}$ is R. In certain embodiments, $R^{3d}$ is S. In certain embodiments, $R^{3d}$ is M.

In certain embodiments, $R^{4d}$ is N. In certain embodiments, $R^{4d}$ is R. In certain embodiments, $R^{4d}$ is H.

In certain embodiments, $R^{5d}$ is S. In certain embodiments, $R^{5d}$ is T.

In certain embodiments, $R^{6d}$ is W. In certain embodiments, $R^{6d}$ is V. In certain embodiments, $R^{6d}$ is F. In certain embodiments, $R^{6d}$ is L. In certain embodiments, $R^{6d}$ is M.

In certain embodiments, $R^{9d}$ is H. In certain embodiments, $R^{9d}$ is S.

In certain embodiments, the peptide comprises an amino acid sequence of formula IV, wherein:
$R^{1d}$ is R;
$R^{2d}$ is R;
$R^{3d}$ is R or S;
$R^{4d}$ is N;
$R^{5d}$ is S;
$R^{6d}$ is W;
$R^{7d}$ is D;
$R^{8d}$ is S; and
$R^{9d}$ is H or S;
or a salt thereof.

In certain embodiments, the peptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to RRRRSVDSH (SEQ ID NO:7). In certain embodiments, the peptide comprises amino acid sequence RRRRSVDSH (SEQ ID NO:7). In certain embodiments, the peptide consists of an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to RRRRSVDSH (SEQ ID NO:7). In certain embodiments, the peptide consists of amino acid sequence RRRRSVDSH (SEQ ID NO:7).

In certain embodiments, the peptide further comprises an amino acid sequence of formula IVa:

$$W^{1d}\text{-}W^{2d}\text{-}W^{3d} \quad \text{(IVa)}$$

or a salt thereof, wherein:
the C'terminus of the amino acid sequence of formula IVa is operably linked to the N'terminus of the amino acid sequence of formula IV;
$W^{1d}$ is R or absent;
$W^{2d}$ is F or absent; and
$W^{3d}$ is R;
or a salt thereof.

In certain embodiments, the peptide further comprises an amino acid sequence of formula IVa, wherein:
$W^{1d}$ is R;
$W^{2d}$ is F; and
$W^{3d}$ is R;
or a salt thereof.

In certain embodiments, the peptide further comprises an amino acid sequence of formula IVa, wherein:
$W^{1d}$ is absent;
$W^{2d}$ is absent; and
$W^{3d}$ is R;
or a salt thereof.

In certain embodiments, $W^{1d}$ is R. In certain embodiments, $W^{1d}$ is absent.

In certain embodiments, $W^{2d}$ is F. In certain embodiments, $W^{2d}$ is absent.

In certain embodiments, the peptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to RRRRRSVDSH (SEQ ID NO:8). In certain embodiments, the peptide comprises amino acid sequence RRRRRSVDSH (SEQ ID NO:8). In certain embodiments, the peptide consists of an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to RRRRRSVDSH (SEQ ID NO:8). In certain embodiments, the peptide consists of amino acid sequence RRRRRSVDSH (SEQ ID NO:8).

In certain embodiments, the peptide further comprises an amino acid sequence of formula IVb:

$$W^{4d}\text{-}W^{5d} \quad \text{(IVb)}$$

wherein:
the C'terminus of the amino acid sequence of formula IV is operably linked to the N'terminus of the amino acid sequence of formula IVb;
$W^{4d}$ is R; and
$W^{5d}$ is absent or S;
or a salt thereof.

In certain embodiments, the peptide further comprises an amino acid sequence of formula IVb, wherein:
$W^{4d}$ is R; and
$W^{5d}$ is S;
or a salt thereof.

In certain embodiments, $W^{5d}$ is absent. In certain embodiments, $W^{5d}$ is S.

Certain embodiments of the invention provide a peptide comprising an amino acid sequence having about 65% to about 100%, about 70% to about 100%, about 71% to about 100%, about 72% to about 100%, about 73% to about 100%, about 74% to about 100%, about 75% to about 100%, about 76% to about 100%, about 77% to about 100%, about 78% to about 100%, about 79% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100% or about 98% to about 100% sequence identity to an amino acid sequence of formula IV. In certain embodiments, the peptide comprises an amino acid sequence having about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula IV. In certain embodiments, the peptide consists of an amino acid sequence having about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to an amino acid sequence of formula IV.

In certain embodiments, the peptide consists of an amino acid sequence of formula IV.

In certain embodiments, the peptide comprises an amino acid sequence of formula IVa, formula IV and formula IVb, wherein the C'terminus of the amino acid sequence of formula IVa is operably linked to the N'terminus of the amino acid sequence of formula IV, and wherein the C'terminus of the amino acid sequence of formula IV is operably linked to the N'terminus of the amino acid of formula IVb.

In certain embodiments, the peptide consists of amino acid sequences of formula IVa, formula IV and formula IVb, wherein the C'terminus of the amino acid sequence of formula IVa is operably linked to the N'terminus of the amino acid sequence of formula IV, and wherein the C'terminus of the amino acid sequence of formula IV is operably linked to the N'terminus of the amino acid of formula IVb.

In certain embodiments, the peptide comprises an amino acid sequence selected using information in FIG. 6.

Certain Modified Peptides of the Invention

In certain embodiments described herein, a peptide of the invention may be modified to enable peptide purification and/or detection, as well as quantification of kinase activity in a particular assay.

For example, in certain embodiments, the peptide further comprises one or more lysine residues (e.g., 1, 2, 3, 4, 5, 6, 7, 8, 9, 10, or more). For example, a peptide described herein may be modified to include one or more lysine residues within the peptide by either insertion or substitution. Alternatively, one or more lysine residues may be added to the N- or C-terminus of the peptide. Atoms within such lysine residues could be used to directly or indirectly link a peptide of the invention to an affinity capture agent (e.g., biotin) or a detectable agent, such as a fluorescent agent or a radioactive agent (e.g., a radionuclide loaded chelating agent).

In certain embodiments, a peptide of the invention comprises an additional amino acid sequence linked to the N- or C-terminus of an amino acid sequence described herein through a peptide bond. In certain embodiments, the second amino acid sequence comprises one or more lysine residues (e.g., GGKGG (SEQ ID NO:9) or GGKKK (SEQ ID NO:10)). For example, in certain embodiments of the invention a peptide as described herein comprises/consists of an amino acid sequence having at least about 80%, 85%, 90%, 95%, 99% or 100% sequence identity to WHLQTWCGYG-GKGG (SEQ ID NO:2) or RRRRRSVDSHGGKGG (SEQ ID NO:1).

In certain embodiments, the additional amino acid sequence encodes a peptide tag (i.e., a fusion protein). In certain embodiments, the peptide tag is a fluorescent protein (e.g., Aquamarine, mCerulean, mTurquoise, mTurquoise2, CyPet, SCFP3A, Amber, mVenus, Ypet, SYFP2, SYFP2A, Clover, LSSmOrgange, mRuby2, ECFP, CFP, YFP, GFP, EGFP, Citrine, EYFP, mCherry or DsRed).

In certain embodiments, the additional amino acid sequence encodes a lanthanide metal binding peptide. Fusion of such a tag to a peptide described herein would enable complexing with a lanthanide metal (e.g., La, Ce, Pr, Nd, Pm, Sm, Eu, Gd, Tb, Dy, Ho, Er, Tm, Yb, and Lu). Peptides that bind lanthanide metals are known in the art (e.g., Sueda et al., Analytical Biochemistry, 422(1):52-54; Martin et al., Methods Mol Biol 1248:201-220 (2015), which are incorporated by reference in their entireties). In certain embodiments, the lanthanide metal binding peptide is a terbium biding peptide (TBP).

In certain embodiments, a peptide as described herein is operably linked to an affinity capture agent. In certain embodiments, the affinity capture agent is biotin. In certain embodiments, the affinity capture agent is operably linked directly or indirectly through a lysine residue. For example, in certain embodiments, an affinity capture agent is operably linked to an additional amino acid sequence comprising one or more lysine residues, wherein the second amino acid sequence is operably linked to the N- or C-terminus of a peptide described herein. For example, as described in Examples 3 and 4, a -GGK$_{biotin}$GG tag (SEQ ID NO:3) was linked to the C-terminus of a series of peptides described herein. Thus, in certain embodiments, a peptide described herein further comprises a -GGK$_{biotin}$GG tag (SEQ ID NO:3) operably linked to the N- or C-terminus of the peptide. In certain embodiments, a peptide as described herein comprises/consists of an amino acid sequence having at least about 80%, 85%, 90%, 95%, 99% or 100% sequence identity to WHLQTWCGYGGK$_{biotin}$GG (SEQ ID NO:12) or RRRRRSVDSHGGK$_{biotin}$GG (SEQ ID NO:11).

In certain embodiments, a peptide as described herein is operably linked to one or more detectable agents. In certain embodiments, when more than one detectable agent is linked to the peptide, the agents may be the same or different.

In certain embodiments, the detectable agent is a radioactive agent. For example, in certain embodiments, the detectable agent comprises a chelating agent. In certain embodiments, the chelating agent is loaded with a radionuclide.

In certain other embodiments, the detectable agent is a fluorescent group, which may also be called a "fluorescent tag" or a "fluorophore". A fluorophore is a molecule that absorbs light (i.e., excites) at a characteristic wavelength and emits light (i.e. fluoresces and emits a signal) at a second lower-energy wavelength. In certain embodiments, the fluorophore is one or more of the fluorophores listed in Table 2.

TABLE 2

| Probe | Excitation (nm) | Emission (nm) |
|---|---|---|
| Hydroxycoumarin | 325 | 386 |
| Alexa fluor | 325 | 442 |
| Aminocoumarin | 350 | 445 |
| Methoxycoumarin | 360 | 410 |
| Cascade Blue | (375); 401 | 423 |
| Pacific Blue | 403 | 455 |
| Pacific Orange | 403 | 551 |
| Lucifer yellow | 425 | 528 |
| Alexa fluor 430 | 430 | 545 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| Red 613 | 480; 565 | 613 |
| PerCP | 490 | 675 |
| Cy2 | 490 | 510 |
| TruRed | 490, 675 | 695 |
| FluorX | 494 | 520 |
| Fluorescein | 495 | 519 |
| FAM | 495 | 515 |
| BODIPY-FL | 503 | 512 |
| TET | 526 | 540 |
| Alexa fluor 532 | 530 | 555 |
| HEX | 535 | 555 |
| TRITC | 547 | 572 |
| Cy3 | 550 | 570 |
| TMR | 555 | 575 |
| Alexa fluor 546 | 556 | 573 |
| Alexa fluor 555 | 556 | 573 |
| Tamara | 565 | 580 |
| X-Rhodamine | 570 | 576 |
| Lissamine Rhodamine B | 570 | 590 |
| ROX | 575 | 605 |
| Alexa fluor 568 | 578 | 603 |
| Cy3.5 581 | 581 | 596 |
| Texas Red | 589 | 615 |
| Alexa fluor 594 | 590 | 617 |
| Alexa fluor 633 | 621 | 639 |
| LC red 640 | 625 | 640 |
| Allophycocyanin (APC) | 650 | 660 |
| Alexa fluor 633 | 650 | 688 |
| APC-Cy7 conjugates | 650; 755 | 767 |
| Cy5 | 650 | 670 |
| Alexa fluor 660 | 663 | 690 |
| Cy5.5 | 675 | 694 |
| LC red 705 | 680 | 710 |
| Alexa fluor 680 | 679 | 702 |
| Cy7 | 743 | 770 |
| IRDye 800 CW | 774 | 789 |
| Alexa Fluor 488 | 490 | 525 |
| Alexa Fluor 647 | 650 | 665 |
| Brilliant Violet 421 | 405 | 421 |

Compositions, Complexes and Kits

Certain embodiments of the invention provide a composition comprising one or more peptides as described herein and a kinase. In certain embodiments, the composition further comprises a detectable agent described herein (e.g., operably linked to the peptide). For example, in certain embodiments, the composition further comprises radio-labeled ATP or a lanthanide metal.

Certain embodiments of the invention provide a composition comprising one or more peptides as described herein and a lanthanide metal. In certain embodiments, the composition further comprises a kinase.

In certain embodiments, the lanthanide metal is selected from the group consisting of La, Ce, Pr, Nd, Pm, Sm, Eu, Gd, Tb, Dy, Ho, Er, Tm, Yb, and Lu. In certain embodiments, the lanthanide metal is Tb.

Certain embodiments of the invention provide a complex comprising one or more peptides as described herein and a lanthanide metal.

In certain embodiments, the lanthanide metal is selected from the group consisting of La, Ce, Pr, Nd, Pm, Sm, Eu, Gd, Tb, Dy, Ho, Er, Tm, Yb, and Lu. In certain embodiments, the lanthanide metal is Tb.

Certain embodiments of the invention provide a kit comprising:

1) a peptide as described herein; and
2) a lanthanide metal;
3) instructions for measuring kinase activity using the peptide and lanthanide metal. In certain embodiments, the kit further comprises one or more kinases.

Methods of Use

As described herein peptides of the invention may be used in an assay to detect kinase activity in a system.

Thus, certain embodiments of the invention provide a method for detecting phosphorylation activity of a kinase, comprising contacting the kinase with peptide as described herein to provide a resulting mixture, wherein phosphorylation of the peptide indicates the kinase is active. In certain embodiments, phosphorylation is detected using an assay described herein.

Certain embodiments of the invention provide a method for detecting phosphorylation activity of a kinase, comprising:

1) contacting the kinase with a peptide as described herein to provide a resulting mixture;
2) measuring a signal from a detectable agent; and
3) detecting phosphorylation activity of the kinase when changes in the signal are detected as compared to a control.

Certain embodiments of the invention provide a method for detecting phosphorylation activity of a kinase, comprising:

1) contacting the kinase with a peptide as described herein to provide a first resulting mixture;
2) measuring a signal from a detectable agent in the first resulting mixture;
3) contacting the kinase with a reference control peptide to provide a second resulting mixture;
4) measuring a signal from a detectable agent in the second resulting mixture; and
5) standardizing the signal from the first resulting mixture using the signal measurements from the second resulting mixture; and
6) detecting phosphorylation activity of the kinase when the standardized signal from the first resulting mixture is changed (e.g., greater) from a reference value.

Certain embodiments of the invention provide a method to identify an inhibitor of a kinase comprising:

1) contacting a peptide as described herein, the kinase and a test compound to provide a resulting mixture;
2) measuring a signal from a detectable agent in the resulting mixture; and
3) identifying the test compound as an inhibitor of the kinase when changes in the signal are detected as compared to a control.

Certain embodiments of the invention provide a method to identify an inhibitor of a kinase comprising:

1) contacting a peptide as described herein and the kinase to provide a first resulting mixture;

2) measuring a signal from a detectable agent in the first resulting mixture;

3) contacting a peptide as described herein, the kinase and a test compound to provide a second resulting mixture;

4) measuring a signal from a detectable agent in the second resulting mixture; and 5) identifying the test compound as an inhibitor of the kinase when changes between the signal in the first resulting mixture and the signal from the second resulting mixture are detected (e.g., the signal from the second resulting mixture is less than or greater than the signal from the first resulting mixture).

In certain embodiments, the detectable agent(s) are operably linked to the peptide.

In certain embodiments, the method further comprises contacting the resulting mixture(s) with the detectable agent. For example, in certain embodiments the detectable agent is radioactive ATP.

In certain embodiments, a signal from the detectable agent(s) is associated with phosphorylation of the peptide by the kinase.

In certain embodiments, the detectable agent is a radioactive agent, a fluorescent agent or a lanthanide metal.

In certain embodiments, activity of the kinase is detected using a lanthanide metal.

Thus, certain embodiments of the invention provide a method for detecting the activity of a kinase comprising:

1) contacting the kinase with a peptide as described herein to provide a resulting mixture;

2) contacting the resulting mixture with a lanthanide metal, under conditions such that a luminescent signal from the lanthanide metal is generated; and 3) detecting the luminescent signal, wherein the luminescent signal correlates with the activity of the kinase.

In certain embodiments, the method further comprises comparing the luminescent signal to a reference luminescent signal, wherein a change in the luminescent signal as compared to the reference luminescent signal is indicative of kinase activity.

In certain embodiments, the method further comprises detecting a reference luminescent signal from a lanthanide metal complexed with a control peptide, wherein the control peptide is non-phosphorylated.

Certain embodiments of the invention also provide a method to identify an inhibitor of a kinase comprising:

1) contacting a peptide as described herein, the kinase, and a test compound to provide a resulting mixture;

2) contacting the resulting mixture with a lanthanide metal; and 3) detecting a luminescent signal from the lanthanide metal, wherein the luminescent signal from the lanthanide metal correlates with the ability of the test compound to inhibit to the kinase.

In certain embodiments, the method further comprises comparing the luminescent signal to a reference luminescent signal, wherein a change in the luminescent signal as compared to the reference luminescent signal indicates the test compound is an inhibitor of the kinase.

In certain embodiments, the peptide described herein and the test compound competitively bind to the kinase.

In certain embodiments, the method further comprises:

4) contacting a peptide as described herein and with the kinase to provide a reference resulting mixture;

5) contacting the reference resulting mixture with a lanthamide metal; and 6) detecting a reference luminescent signal from the lanthanide metal, wherein the reference luminescent signal from the lanthanide metal correlates with the activity of the kinase.

In certain embodiments, the peptide and the test compound competitively bind to the kinase.

Certain embodiments of the invention provide a method to determine if a kinase is active in a system comprising: determining whether a peptide as described herein has served as a substrate for kinase activity, wherein such a positive indication of activity indicates that the kinase is active in the system.

In certain embodiments of a method described herein, the kinase is Liver Kinase B1 (LKB1), AMP-activated protein kinase (AMPK), mechanistic target of rapamycin serine/threonine kinase (mTOR) or protein kinase B (Akt).

In certain embodiments, the kinase is LKB1 and the peptide comprises an amino acid sequence of formula I.

In certain embodiments, the kinase is AMPK and the peptide comprises an amino acid sequence of formula II.

In certain embodiments, the kinase is mTOR and the peptide comprises an amino acid sequence of formula III.

In certain embodiments, the kinase is Akt and the peptide comprises an amino acid sequence of formula IV.

In certain embodiments of a method described herein, the luminescent signal is detected by luminescence spectroscopy.

In certain embodiments of a method described herein, the luminescent signal is detected by time-resolved luminescence spectroscopy.

In certain embodiments of a method described herein, the kinase is in a cell.

In certain embodiments, the cell is a human cell. In certain embodiments, the human cell is derived from human bone marrow or human blood.

In certain embodiments, the cell is a cancer cell. In certain embodiments, the cancer is leukemia (e.g., chronic myeloid leukemia). In certain embodiments, the cell is a drug-resistant cancer cell.

Certain embodiments of the invention provide a method to design a biosensor which detects the activity of a first kinase comprising:

1) generating a candidate set comprising the peptides described herein;

2) excluding one or more peptides from the candidate set, which are likely to bind a kinase that is not the first kinase; and 3) screening the remaining peptides from step 2) for the ability to form a complex with a lanthanide metal.

In certain embodiments, a lanthanide metal gives a differentiable luminescent readout when the peptide is phosphorylated.

In certain embodiments of the invention, a peptide described herein may be used in an assay to determine if a specific kinase is active in a system.

In certain embodiments, a peptide described herein may be used in assays to identify inhibitors of certain kinases.

In certain embodiments, a peptide described herein may be used in a LRET assay, similar to those described in United States Patent Application Publication Number US2016/0097084, the content of which is hereby incorporated herein in its entirety.

Certain Definitions

The term "complex" refers to molecules or ensembles that consist of a central atom or ion, which is usually metallic, and a surrounding array of bound molecules, ions or moieties of a molecule. The surrounding array of bound molecules, ions or moieties of a molecule are usually electron donors attracted to the central atom or ion. The surrounding array of bound molecules, ions or moieties of a molecule are usually neutral or negatively charged.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucl. Acids Res., 19:508; Ohtsuka et al. (1985) JBC, 260:2605; Rossolini et al. (1994) Mol. Cell. Probes, 8:91. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$) alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

The terms "protein," "peptide" and "polypeptide" are used interchangeably herein. Polypeptide sequences specifically recited herein are written with the amino terminus on the left and the carboxy terminus on the right.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

"Wild-type" refers to the normal gene, or organism found in nature without any known mutation.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, Molecular Cloning: A Laboratory Manual, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

A "vector" is defined to include, inter alia, any viral vector, plasmid, cosmid, phage or binary vector in double or single stranded linear or circular form which may or may not be self-transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more sequences (e.g., nucleic acids, polynucleotides or polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA, gene sequence or peptide sequence, or the complete cDNA, gene sequence or peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS, 4:11; the local homology algorithm of Smith et al. (1981) Adv. Appl. Math. 2:482; the homology alignment algorithm of Needleman and Wunsch, (1970) JMB, 48:443; the search-for-similarity-method of Pearson and Lipman, (1988) Proc. Natl. Acad. Sci. USA, 85:2444; the algorithm of Karlin and Altschul, (1990) Proc. Natl. Acad. Sci. USA, 87:2264, modified as in Karlin and Altschul, (1993) Proc. Natl. Acad. Sci. USA, 90:5873.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237; Higgins et al. (1989) CABIOS 5:151; Corpet et al. (1988) Nucl. Acids Res. 16:10881; Huang et al. (1992) CABIOS 8:155; and Pearson et al. (1994) Meth. Mol. Biol. 24:307. The ALIGN program is based on the algorithm of Myers and Miller, supra. The BLAST programs of Altschul et al. (1990) JMB, 215:403; Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm-.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of sequences for determination of percent sequence identity to another sequence may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel (1985) Proc. Natl. Acad. Sci. USA 82:488; Kunkel et al. (1987) Meth. Enzymol. 154:367; U.S. Pat. No. 4,873,192; Walker and Gaastra (1983) Techniques in Mol. Biol. (MacMillan Publishing Co., and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. In certain embodiments, the deletions, insertions, and substitutions of the polypeptide sequence encompassed herein may not produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

"Operably-linked" refers to the association two chemical moieties so that the function of one is affected by the other, e.g., an arrangement of elements wherein the components so described are configured so as to perform their usual function. In certain embodiments, amino acid sequences are operably linked via a peptide bond.

In certain embodiments, a peptide of the invention is operably linked to an affinity capture agent or a detectable agent. The nature of the linkage is not critical provided the resulting conjugate retains the useful biological properties described herein (e.g., the peptide functions as a kinase substrate and the detectable or affinity capture agent retains its functionality).

In certain embodiments, the peptide is linked to the detectable agent or affinity capture agent through a direct bond.

In certain embodiments, the peptide is linked to the detectable agent or affinity capture agent through a linking group.

In one embodiment of the invention the linking group has a molecular weight of from about 20 daltons to about 20,000 daltons. In one embodiment of the invention the linking group has a molecular weight of from about 20 daltons to about 5,000 daltons. In one embodiment of the invention the linking group has a molecular weight of from about 20 daltons to about 1,000 daltons. In one embodiment of the invention the linking group has a molecular weight of from about 20 daltons to about 200 daltons.

In another embodiment of the invention the linking group has a length of about 5 angstroms to about 60 angstroms.

In another embodiment of the invention the linking group is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or a divalent ring of formula:

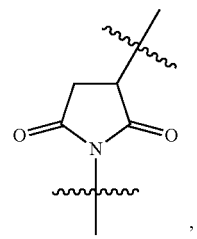 [SMILES: *C1CC(=O)N(*)C1=O]

and wherein the chain or ring is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In another embodiment of the invention a carboxylic acid of the detectable agent or affinity capture agent is reacted with an amine of the peptide to form an amide bond.

The invention will now be illustrated by the following non-limiting Examples.

Example 1

Metabolic Pathway Comparison Profiling

Figure 2:
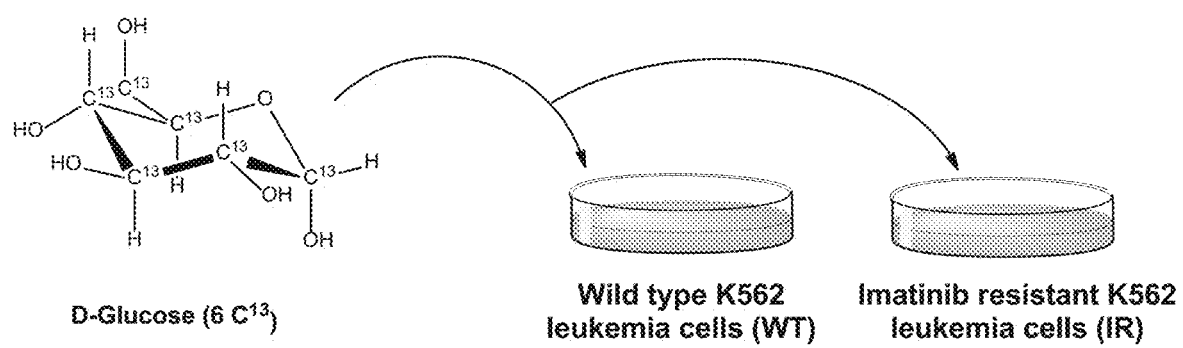
FIG. 2 illustrates the metabolic pathway comparison profiling experiment. Media containing 6-$C^{13}$ labeled D-glucose was added to the wild type K562 leukemia cells and imatinib resistant K562 leukemia cells, respectively.

A metabolomic analysis was undertaken to compare and quantify small molecule metabolite differences between wild type leukemia cells and those specifically cultured for resistance to imatinib (Gleevec), the first-line clinical treatment for CIVIL. Media containing 6-$C^{13}$ labeled D-glucose was added to the cells for a 12 hour treatment before the metabolites were harvested (FIG. 2).

Increased relative amounts of glycolysis and PPP intermediates as well as increased $C^{13}$ labeling (i.e. glucose 6-phosphate and fructose 6-phosphate) in the drug-resistant (IR) versus wild type (WT) leukemia lines illustrate increased reliance on these metabolic pathway alterations in this system. The relative amount and labeling of citric acid cycle metabolites is relatively unchanged to slightly decreased in the drug-resistant line for most intermediates. Results indicate an increased reliance on the glycolysis and pentose phosphate pathways for energy production in the drug-resistant cell type, with a corresponding increase in $C^{13}$ labeling in several of the respective pathway intermediates.

Example 2

KINATEST-ID Workflow

The KINATEST-ID platform is unique in its comparison and filtering capabilities of libraries of candidate biosensor sequences. This enables development of favorable and highly selective biosensors which are compatible with cells and high throughput detection in multi-well plates (terbium luminescence). Specifically, this platform for rational biosensor design winnows an input set of potential substrate sequences for a specific kinase of interest collected from careful curation of literature and online databases to an output set of potential candidate sequences for biosensor development based on a statistical analysis of which amino acids are most favored at positions −7 to +7, as well as at positions −4 to +4, immediately surrounding the substrate serine/threonine. This candidate set is then filtered to specifically exclude sequences, e.g., sequences likely to bind irrelevant kinases to ensure specificity. For example, sequences may be further processed with the Screener and Aligner tools before synthesis and empirical testing. Finally, the remaining sequences are screened for the ability to bind terbium which allows for a differentiable luminescent readout if the substrate phosphosite, which acts as a sensor to enhance the lanthanide signal, is phosphorylated or not.

Biosensors for the four metabolically-relevant serine/threonine kinases (LKB1, AMPK, mTOR, and Akt) are developed based on this process. These biosensors may be used to measure and quantify signaling activity of these kinases in cells, such as cancer cells, including wild type CML and a drug-resistant model CIVIL lines. Signaling differences could provide insight into how these metabolic alterations manifest themselves, whether these differences can help leukemia cells survive stressful conditions, and the onset of off-target drug-resistance in this system. These biosensors may also be used in high throughput drug screens to discover inhibitors of these kinases. Additionally, they could be used to test kinase activity in drug-resistant patient samples for clinical diagnostics.

Example 3

Development of a Biosensor for Akt

As described herein, a biosensor for the Akt serine/threonine kinase was discovered using the KINATEST-ID pipeline. This peptide sequence, RRRRRSVDSHGGK$_{biotin}$GG (SEQ ID NO:11), is an artificial substrate for this kinase. This sequence was discovered through an analysis of the amino acid preferences of Akt and was then synthesized in-lab (with a C-terminal-GGK$_{biotin}$GG tag (SEQ ID NO:3) for affinity purification purposes).

Materials and Methods

The in vitro kinase assay was performed with Akt and Aktide biosensor (RRRRRSVDSHGGK$_{biotin}$GG (SEQ ID NO:11)). First, the kinase (15 nM final concentration) was pre-incubated in kinase reaction buffer (10 mM HEPES, 10 mM MgCl$_2$, 0.125 ng/µL BSA, 100 µM adenosine triphosphate (ATP), pH 7.5) for 15 minutes. Then the substrate peptide, Aktide (20 µM final concentration), was added and the reaction was kept at 37° C. The reaction was monitored at different time points by removing 20 µL aliquots and quenching with 10 µL of 6 M urea at 0, 30, 60, and 120 minutes. The samples were then desalted with C$_{18}$ zip tips according to the manufacturer's protocol and analyzed on an Applied Biosystems-Sciex 5800 MALDI/TOF/TOF-MS.

Results and Discussion

Figure 7:
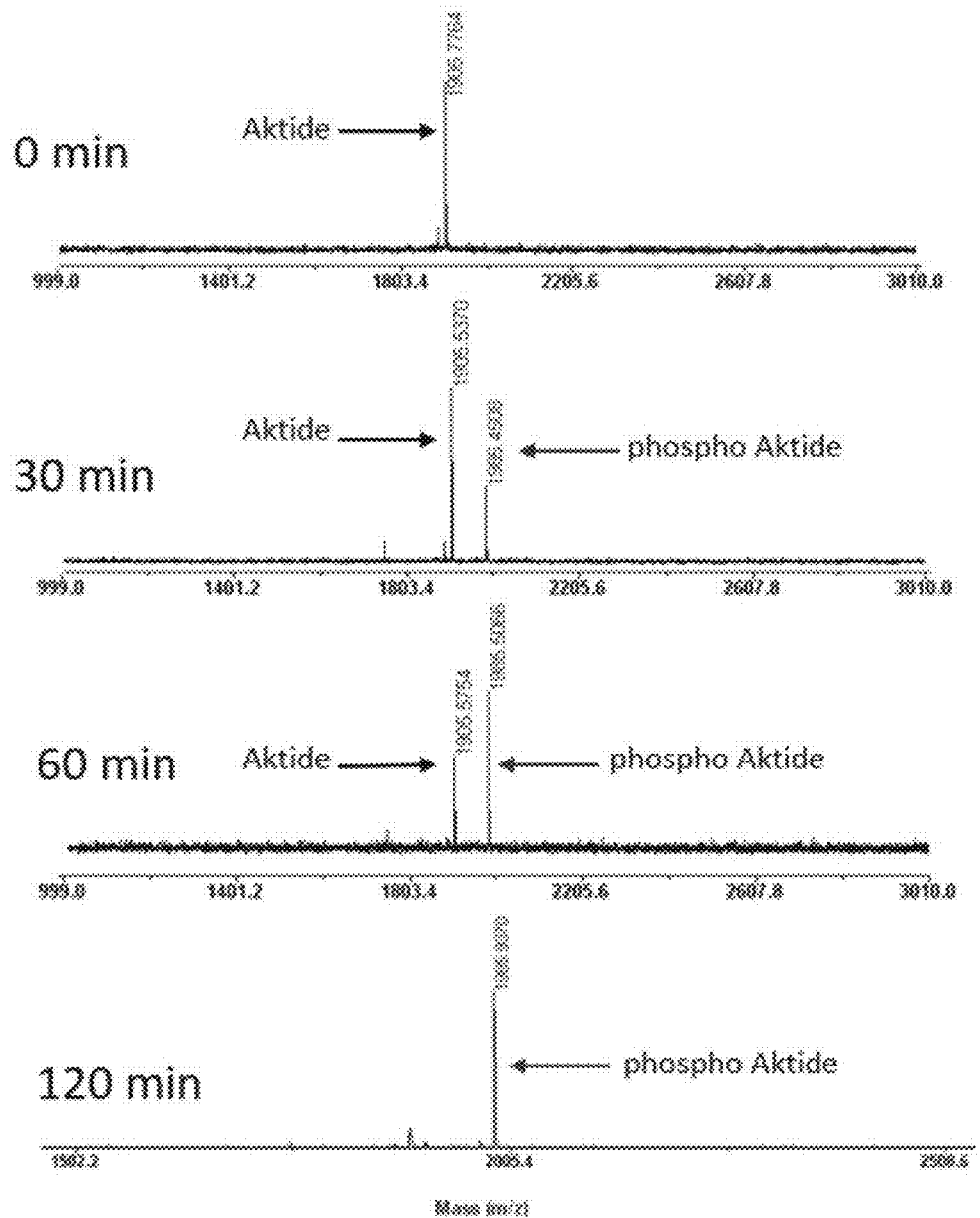
FIG. 7. These data show the results of a time-course kinase assay with Akt and the biosensor peptide substrate RRRRRSVDSHGGK$_{biotin}$GG (SEQ ID NO:11). The abundance of the biosensor (labeled "Aktide") and its phosphorylated version (labeled "phospho Aktide") are shown over four different time points (0, 30, 60, 120 min) which represent the amount of time the peptide was incubated with the kinase. Nearly complete conversion to phosphorylated product was observed after 2 hr.

The data in FIG. 7 show that this peptide sequence is able to be efficiently phosphorylated by Akt over a 2 hr kinase assay.

Example 4

Development of a Biosensor for LKB1

Described herein is the development of a biosensor for the LKB1 serine/threonine kinase Specifically, an initial screen was performed with six candidate biosensors peptides, wherein the peptides were evaluated in kinase assays using LKB1. These six sequences were several of the top scoring peptides predicted to be LKB1 substrates through the KINATEST-ID pipeline, based on its amino acid preferences. Out of these six, one sequence, WHLQTWCGYG-GK$_{biotin}$GG (SEQ ID NO:12), was shown to be partially phosphorylated by LKB1 after a 3 hr reaction.

Materials and Methods

The in vitro kinase assay screen was performed with LKB1 and the candidate biosensor sequence (WHLQTW-CGYGGK$_{biotin}$GG (SEQ ID NO:12)). First the kinase, (15 nM final concentration), was pre-incubated in kinase reaction buffer (10 mM HEPES, 10 mM MgCl$_2$, 0.125 ng/µL BSA, 100 µM adenosine triphosphate (ATP), pH 7.5) for 15 minutes. Then the substrate peptide, (20 µM final concentration), was added and the reaction was kept at 37° C. The reaction was quenched with 6 M urea and then the sample was desalted with C$_{18}$ zip tips according to the manufacturer's protocol and analyzed on an Agilent 1200 series LC and Agilent 6130 quadrupole ESI-MS.

Results and Discussion

Figure 8A:
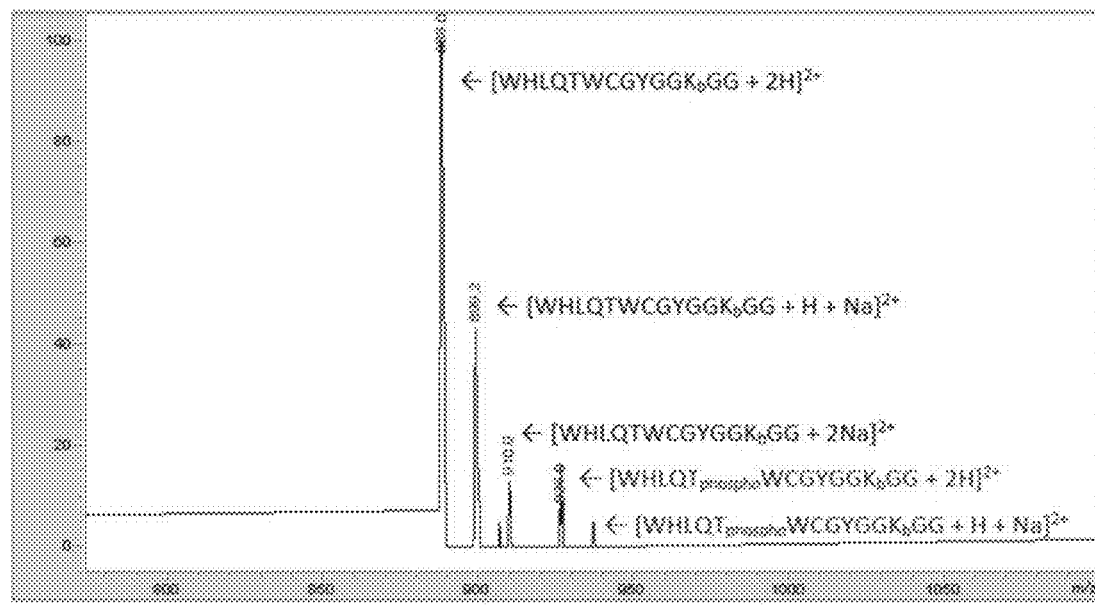
FIGS. 8A-B.
Figure 8B:
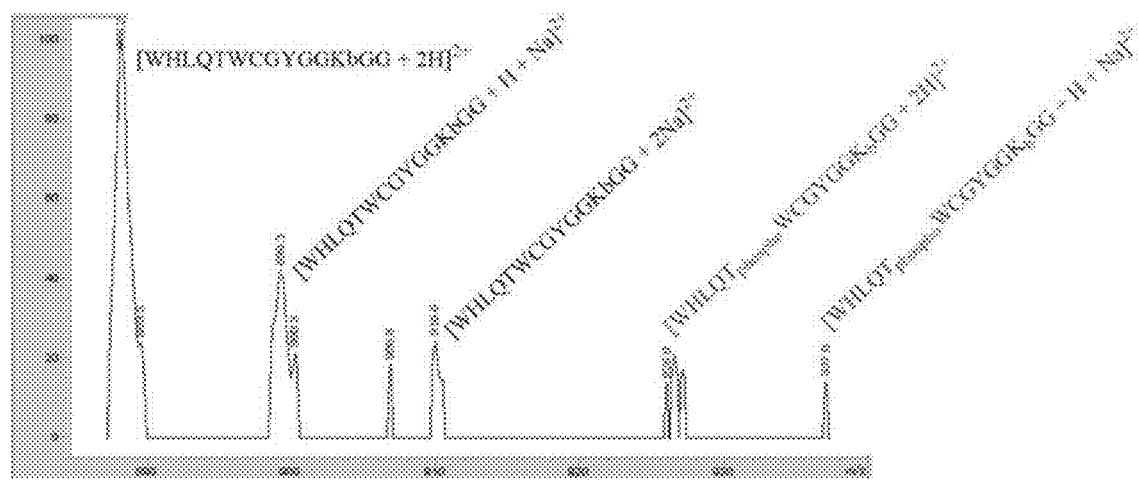

The data in FIGS. 8A-8B shows that this initial peptide sequence is able to be partially phosphorylated by LKB1 after a 3 hr reaction. This sequence may be used as a scaffold from which to construct a second generation library to optimize LKB1 substrate activity and kinase assay conditions. The second generation of peptides may contain peptides which comprise consensus sequence XXLQTXCGX (SEQ ID NO:4) (e.g. WHLQTWCGS (SEQ ID NO:5)). Additionally, information from the other five peptides may be used to further refine the consensus sequence. For example, the other five peptides were sequences with high similarity to the one shown in FIGS. 8A-8B but with one or two amino acid site changes. These differing amino acids may be examined to identify which of these changes abolishes activity. This optimization may be performed by one skilled in the art, guided by the sequence libraries and amino acid preferences generated from the KINATEST-ID pipeline and the in vitro validation experiments.

CONCLUSION

Steps similar to those described in the above Examples may be used to further develop new biosensors for the AMPK and mTOR kinases. The biosensors described herein may be used to measure the signaling activity of these kinases in different settings (e.g. in drug-sensitive versus drug-resistant chronic myeloid leukemia K562 cell lines).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A peptide comprising amino acid sequence WHLQTWCGS (SEQ ID NO:5) or WHLQTWCGY (SEQ ID NO:6), or a salt thereof.

2. The peptide of claim 1, comprising amino acid sequence WHLQTWCGS (SEQ ID NO:5).

3. The peptide of claim 1, comprising amino acid sequence WHLQTWCGY (SEQ ID NO:6).

4. The peptide of claim 1, further comprising the amino acid sequence of formula Ia:

$$W^{1a}\text{-}W^{2a}\text{-}W^{3a} \qquad (Ia)$$

and/or the amino acid sequence of formula Ib:

$$W^{4a}\text{-}W^{5a}\text{-}W^{6a} \qquad (Ib)$$

wherein:
the C'terminus of the amino acid sequence of formula Ia is operably linked to the N'terminus of the amino acid sequence of formula I;
the C'terminus of the amino acid sequence of formula I is operably linked to the N'terminus of the amino acid sequence of formula Ib;
$W^{1a}$ is selected from the group consisting of: absent, H, K, Q, T, and V;
$W^{2a}$ is selected from the group consisting of: absent, D, G, P, V, and W;
$W^{3a}$ is selected form from the group consisting of: D and G;
$W^{4a}$ is selected from the group consisting of: L and P;
$W^{5a}$ is selected from the group consisting of: absent, H and P; and
$W^{6a}$ is absent or Y;
or a salt thereof.

5. A composition comprising one or more peptides of claim 1, a kinase, and optionally, a lanthanide metal.

6. The peptide of claim 1, consisting of amino acid sequence WHLQTWCGS (SEQ ID NO:5), or a salt thereof.

7. The peptide of claim 1, consisting of amino acid sequence WHLQTWCGY (SEQ ID NO:6), or a salt thereof.

8. A peptide comprising the amino acid sequence of formula I:

$$R^{1a}\text{-}R^{2a}\text{-}R^{3a}\text{-}R^{4a}\text{-}R^{5a}\text{-}R^{6a}\text{-}R^{7a}\text{-}R^{8a}\text{-}R^{9a} \qquad (I)$$

wherein:
the peptide is a Liver Kinase B1 (LKB1) substrate;
$R^{1a}$ is W;
$R^{2a}$ is selected from the group consisting of: F, H, K, and L;
$R^{3a}$ is L;
$R^{4a}$ is selected from the group consisting of: D, M, Q, T, and Y;
$R^{5a}$ is T;
$R^{6a}$ is selected from the group consisting of: C, F, S, and W;
$R^{7a}$ is C;
$R^{8a}$ is selected from the group consisting of: G and I; and
$R^{9a}$ is selected from the group consisting of: S, T, and Y;
or a salt thereof.

9. The peptide of claim 8, wherein:
$R^{1a}$ is W;
$R^{2a}$ is selected from the group consisting of: F, H, K, and L;
$R^{3a}$ is L;
$R^{4a}$ is Q;
$R^{5a}$ is T;
$R^{6a}$ is selected from the group consisting of: C, F, S, and W;
$R^{7a}$ is C;
$R^{8a}$ is G; and
$R^{9a}$ is selected from the group consisting of: S, T, and Y;
or a salt thereof.

10. The peptide of claim 8, wherein:
$R^{1a}$ is W;
$R^{2a}$ is F, K or L;
$R^{3a}$ is L;
$R^{4a}$ is D or Q;
$R^{5a}$ is T;
$R^{6a}$ is F, S or W;
$R^{7a}$ is C;
$R^{8a}$ is G; and
$R^{9a}$ is T or S;
or a salt thereof.

11. The peptide of claim 8, wherein $R^{2a}$ is K.
12. The peptide of claim 8, wherein $R^{4a}$ is Q.
13. The peptide of claim 8, wherein $R^{6a}$ is W.
14. The peptide of claim 8, wherein $R^{8a}$ is G.
15. The peptide of claim 8, wherein $R^{9a}$ is S.
16. The peptide of claim 8, wherein the peptide is nine amino acids in length.
17. The peptide of claim 8, further comprising the amino acid sequence of formula Ia:

$$W^{1a}\text{-}W^{2a}\text{-}W^{3a} \qquad (Ia)$$

and/or the amino acid sequence of formula Ib:

$$W^{4a}\text{-}W^{5a}\text{-}W^{6a} \qquad (Ib)$$

wherein:
the C'terminus of the amino acid sequence of formula Ia is operably linked to the N'terminus of the amino acid sequence of formula I;

the C'terminus of the amino acid sequence of formula I is operably linked to the N'terminus of the amino acid sequence of formula Ib;

$W^{1a}$ is selected from the group consisting of: absent, H, K, Q, T, and V;

$W^{2a}$ is selected from the group consisting of: absent, D, G, P, V, and W;

$W^{3a}$ is selected from the group consisting of: D and G;

$W^{4a}$ is selected from the group consisting of: L and P;

$W^{5a}$ is selected from the group consisting of: absent, H and P; and $W^{6a}$ is absent or Y;

or a salt thereof.

18. A composition comprising one or more peptides of claim 8, a kinase, and optionally, a lanthanide metal.

* * * * *

SEQUENCE LISTING

<160> NUMBER OF SEQ ID NOS: 14

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Arg Arg Arg Ser Val Asp Ser His Gly Gly Lys Gly Gly
1               5                  10                  15

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp His Leu Gln Thr Trp Cys Gly Tyr Gly Gly Lys Gly Gly
1               5                  10

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys-biotin

<400> SEQUENCE: 3

Gly Gly Lys Gly Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 4

Xaa Xaa Leu Gln Thr Xaa Cys Gly Xaa
1               5

<210> SEQ ID NO 5
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 5

Trp His Leu Gln Thr Trp Cys Gly Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp His Leu Gln Thr Trp Cys Gly Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Arg Arg Ser Val Asp Ser His
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Arg Arg Arg Arg Ser Val Asp Ser His
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Lys Gly Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Lys Lys Lys
1               5
```

```
<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Lys-biotin

<400> SEQUENCE: 11

Arg Arg Arg Arg Arg Ser Val Asp Ser His Gly Gly Lys Gly Gly
1               5                  10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys-biotin

<400> SEQUENCE: 12

Trp His Leu Gln Thr Trp Cys Gly Tyr Gly Gly Lys Gly Gly
1               5                  10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Met, Arg or Ser
<220> FEATURE:
<221> NAME/KEY: MOD_RES
<222> LOCATION: (4)..(4)
<223> OTHER INFORMATION: His, Asn or Arg
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Phe, Leu, Met, Val or Trp
<220> FEATURE:
<221> NAME/KEY: MOD_RES
<222> LOCATION: (9)..(9)
<223> OTHER INFORMATION: His or Ser
<220> FEATURE:
<223> OTHER INFORMATION: See specification as filed for detailed
      description of substitutions and preferred embodiments

<400> SEQUENCE: 13

Arg Arg Xaa Xaa Xaa Xaa Asp Ser Xaa
1               5

<210> SEQ ID NO 14
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phospho-Thr
<220> FEATURE:
<221> NAME/KEY: MOD_RES
<222> LOCATION: (12)..(12)
<223> OTHER INFORMATION: Lys-biotin

<400> SEQUENCE: 14

Trp His Leu Gln Thr Trp Cys Gly Tyr Gly Gly Lys Gly Gly
1               5                   10
```